US010689664B2

(12) United States Patent
Mittendorf et al.

(10) Patent No.: US 10,689,664 B2
(45) Date of Patent: Jun. 23, 2020

(54) NUCLEIC ACID MOLECULE FOR CONFERRING INSECTICIDAL PROPERTIES IN PLANTS

(71) Applicant: SYNGENTA PARTICIPATIONS AG, Basel (CH)

(72) Inventors: Volker Mittendorf, Research Triangle Park, NC (US); Jared Conville, Research Triangle Park, NC (US); John Daniel Hipskind, Research Triangle Park, NC (US); Kasimalai Azhakanandam, Research Triangle Park, NC (US); Andrew Noe, Clinton, IL (US); Xiaoyin Fei, Research Triangle Park, NC (US); Kevin V. Donohue, Research Trianlge Park, NC (US)

(73) Assignee: Syngenta Participations AG, Basel (CH)

( * ) Notice: Subject to any disclaimer, the term of this patent is extended or adjusted under 35 U.S.C. 154(b) by 118 days.

(21) Appl. No.: 15/569,096

(22) PCT Filed: Apr. 27, 2016

(86) PCT No.: PCT/US2016/029424
§ 371 (c)(1),
(2) Date: Oct. 25, 2017

(87) PCT Pub. No.: WO2016/209360
PCT Pub. Date: Dec. 29, 2016

(65) Prior Publication Data
US 2018/0111969 A1   Apr. 26, 2018

Related U.S. Application Data

(60) Provisional application No. 62/184,227, filed on Jun. 24, 2015.

(51) Int. Cl.
*C07K 14/325* (2006.01)
*C12N 15/82* (2006.01)
*A01H 1/02* (2006.01)

(52) U.S. Cl.
CPC .......... *C12N 15/8286* (2013.01); *A01H 1/02* (2013.01); *C07K 14/325* (2013.01); *Y02A 40/162* (2018.01)

(58) Field of Classification Search
CPC .......................... C12N 15/8286; C07K 14/325
See application file for complete search history.

(56) References Cited

U.S. PATENT DOCUMENTS

| 5,994,629 | A | * | 11/1999 | Bojsen | A01H 5/12 435/419 |
| 7,030,295 | B2 | * | 4/2006 | Chen | C12N 15/8286 800/302 |
| 7,230,167 | B2 | | 6/2007 | Chen et al. | |
| 7,276,583 | B2 | | 10/2007 | Chen et al. | |
| 7,282,355 | B2 | | 10/2007 | Shi | |
| 7,569,363 | B2 | | 8/2009 | Chen et al. | |
| 8,008,248 | B2 | | 8/2011 | Chen et al. | |
| 8,216,806 | B2 | | 7/2012 | Chen et al. | |
| 8,247,369 | B2 | | 8/2012 | Chen et al. | |
| 8,309,516 | B2 | * | 11/2012 | Hart | C07K 14/325 514/4.5 |
| 8,466,346 | B2 | | 6/2013 | DeFramond et al. | |
| 8,541,655 | B2 | | 9/2013 | Chen et al. | |
| 8,759,620 | B2 | | 6/2014 | Chen et al. | |
| 9,133,474 | B2 | | 9/2015 | De Framond et al. | |
| 9,522,937 | B2 | | 12/2016 | Hart et al. | |
| 10,100,371 | B2 | | 10/2018 | De Framond et al. | |
| 2005/0039226 | A1 | | 2/2005 | Barbour et al. | |
| 2011/0151441 | A1 | | 6/2011 | Chen et al. | |
| 2012/0174267 | A1 | | 7/2012 | De Framond et al. | |

FOREIGN PATENT DOCUMENTS

| WO | 2003018810 A2 | 3/2003 |
| WO | 2003078587 A2 | 9/2003 |
| WO | 2008121633 A1 | 10/2008 |
| WO | 2010077816 A1 | 7/2010 |
| WO | 2015056080 A1 | 4/2015 |

OTHER PUBLICATIONS

Bravo, A., & Soberón, M. (2008). How to cope with insect resistance to Bt toxins?. Trends in biotechnology, 26(10), 573-579. (Year: 2008).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Hibbard, Bruce E., et al. "Mortality impact of Bt transgenic maize roots expressing eCry3. 1Ab, mCry3A, and eCry3. 1Ab plus mCry3A on western corn rootworm larvae in the field." Journal of economic entomology 104.5 (2011): 1584-1591 (Year: 2011).*
Frank, Daniel L., et al. "Effect of seed blends and soil-insecticide on western and northern corn rootworm emergence from mCry3A + eCry3. 1Ab Bt maize." Journal of economic entomology 108.3 (2015): 1260-1270. (Year: 2015).*
Hibbard, Bruce E., et al. "Mortality impact of Bt transgenic maize roots expressing eCry3. 1Ab, mCry3A, and eCry3. 1Ab plus mCry3A on western corn rootworm larvae in the field." Journal of economic entonnology 104.5 (2011): 1584-1591 (Year : 2011).*
Extended European Search Report for EP Application No. 16814863.3 dated Nov. 2, 2018.
Frank, D.L. et al, "Effect of Seed Blends and Soil-Insecticide on Western and Northern Corn Rootworm Emergence from mCry3A + eCry3.1Ab Bt Maize," J. Econ Entomol, Apr. 24, 2015, vol. 108, No. 3, pp. 1260-1270.

(Continued)

*Primary Examiner* — Lee A Visone
(74) *Attorney, Agent, or Firm* — Karen A. Magri

(57) ABSTRACT

The present invention is drawn to a nucleic acid sequence which confers expression of the insecticidal proteins mCry3A and eCry3.1Ab when introduced into a cell.

22 Claims, 1 Drawing Sheet
Specification includes a Sequence Listing.

(56) References Cited

OTHER PUBLICATIONS

International Search Report dated Aug. 5, 2016 for International Application No. PCT/US16/29424.
Hibbard et al., J. Econ Entomol., Oct. 2011, vol. 104, No. 5, pp. 1584-91.

* cited by examiner

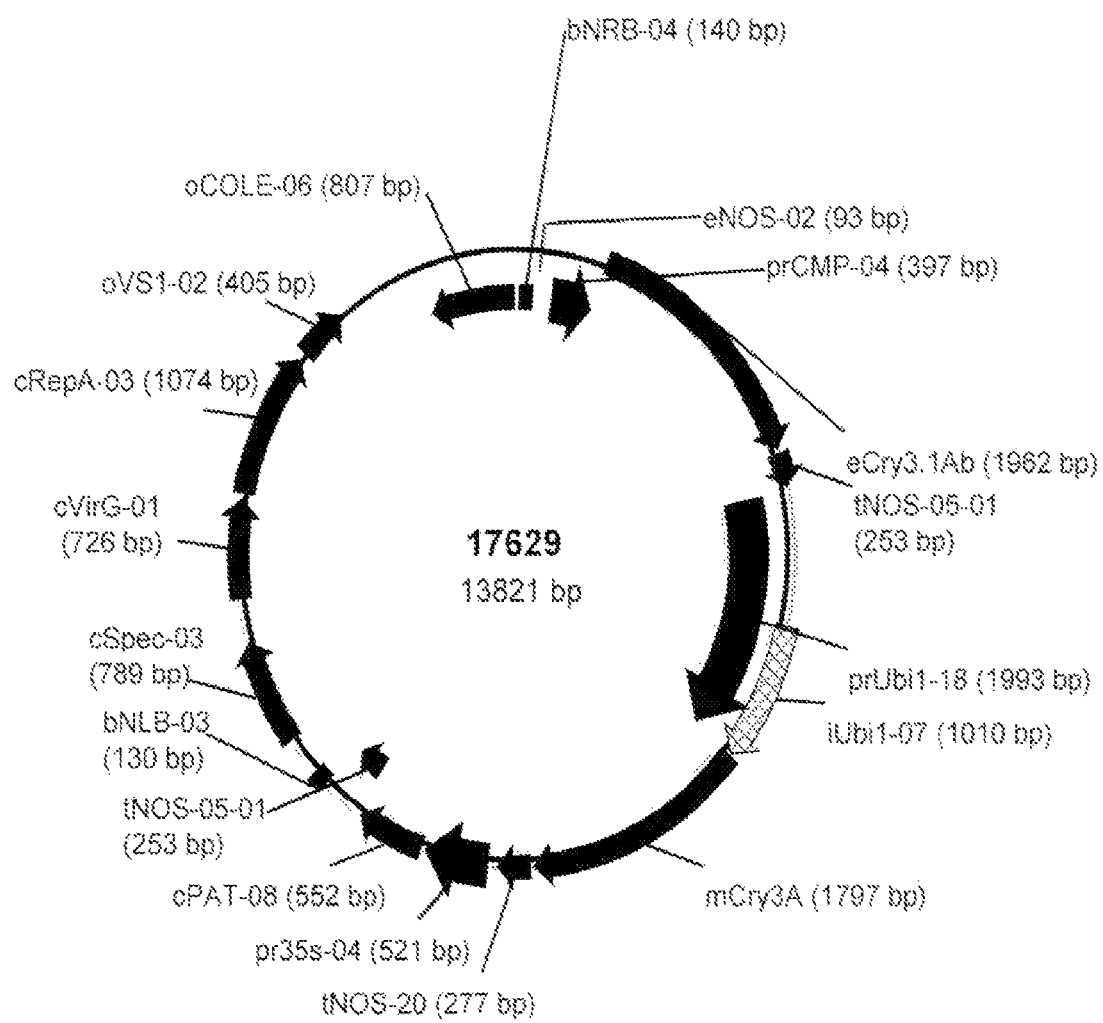

US 10,689,664 B2

NUCLEIC ACID MOLECULE FOR CONFERRING INSECTICIDAL PROPERTIES IN PLANTS

RELATED APPLICATIONS

This application claims the benefit of provisional application 62/184,227 filed Jun. 24, 2015 and incorporated by reference in its entirety herein.

STATEMENT REGARDING ELECTRONIC SUBMISSION OF A SEQUENCE LISTING

A sequence listing in ASCII text format, submitted under 37 C.F.R. § 1.821, entitled 80823 ST25.txt", 30 kilobytes in size, generated on Apr. 21, 2016 and filed via EFS-Web is provided in lieu of a paper copy. This sequence listing is hereby incorporated by reference into the specification for its disclosures.

FIELD OF THE INVENTION

The present invention generally relates to a nucleic acid sequence which confers expression of the insecticidal proteins mCry3A and eCry3.1Ab when introduced into a cell.

BACKGROUND OF THE INVENTION

Plant pests are a major factor in the loss of the world's important agricultural crops. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

*Bacillus thuringiensis* (Bt) Cry proteins (also called 5-endotoxins) are proteins that form a crystalline matrix in *Bacillus* that are known to possess insecticidal activity when ingested by certain insects. Genes coding for Cry proteins have been isolated and their expression in crop plants have been shown to provide another tool for the control of economically important insect pests. Such transgenic plants expressing the Cry proteins have been commercialized, allowing farmers to reduce or augment applications of chemical insect control agents. Coleopteran-active Cry proteins useful in transgenic plants include, for example, Cry3A, Cry3B and the Cry34/Cry35 complex.

Although the usage of transgenic plants expressing Cry proteins is another tool in the insect control toolbox, it is still susceptible to resistance breakdown. Insect pests that now have resistance against the Cry proteins expressed in certain transgenic plants are known. A strategy to reduce the chances of resistance breakdown is to "stack" transgenic traits with different modes of action against the same insect pest species in a single plant. Currently, transgenic traits are frequently stacked through breeding and subsequent screening to get multiple transgenic traits in a single commercial germplasm. These breeding and screening steps are required for every variety of germplasm into which introduction of these two traits is desirable. For many agronomically important crops, such as corn, these two traits need to be maintained as hybrids for dozens of germplasm varieties. Additionally, factors such as the genetic linkage of undesirable traits or genetic recombination may complicate the introduction of two traits from two distinct loci into a single germplasm variety. Therefore, it would be advantageous to create a nucleic acid molecule which carries multiple insecticidal traits and can be introduced at a single locus in the genome of the transgenic plant.

SUMMARY OF THE INVENTION

The present invention provides a nucleic acid molecule that is at least 90% identical, at least 95% identical, at least 97% identical, at least 98% identical, at least 99% identical, or 100% identical to SEQ ID NO: 1. The present invention also provides for a nucleic acid molecule, a chimeric nucleic acid molecule, and/or a recombinant nucleic acid construct or vector which comprise, consist, or consist essentially of SEQ ID NO: 1. The present invention also provides for a nucleic acid molecule, a chimeric nucleic acid molecule, and/or a recombinant nucleic acid construct or vector which comprise, consist, or consist essentially of a nucleic acid sequence that is at least 90% identical, at least 95% identical, at least 97% identical, at least 98% identical, at least 99% identical, or 100% identical to SEQ ID NO: 1.

The present invention also provides for use of a nucleic acid molecule of the invention as described herein, wherein expression of said nucleic acid molecule in a cell confers enhanced insecticidal properties.

The present invention also provides for a transgenic host cell comprising a nucleic acid molecule of the invention as described herein. The transgenic host cell described above may be any suitable prokaryotic or eukaryotic cell, e.g., a bacterial cell or a plant cell. In representative embodiments, the transgenic bacterial cell may be an *Escherichia coli*, a *Bacillus* (e.g., *B. thuringiensis*, *B. subtilis*, *B. megaterium*; *B. cereus*, and the like), an *Agrobacterium* ssp. or a *Pseudomonas* ssp. cell. The transgenic plant cell may be found within a transgenic plant, plant part, plant tissue, or plant cell culture. The transgenic plant may be a monocotyledonous or dicotyledonous plant. The transgenic plant may be from a plant species including but not limited to maize, sorghum, wheat, sunflower, tomato, crucifers, oat, turf grass, pasture grass, peppers, potato, cotton, rice, soybean, sugarcane, sugar beet, tobacco, barley, or oilseed rape.

The present invention also provides for a progeny of any generation of a transgenic plant, wherein said transgenic plant comprises a nucleic acid molecule of the invention as described herein. The present invention also provides for a transgenic seed and for a transgenic propagule from said transgenic plant.

The present invention also provides for a method of producing a transgenic plant with enhanced insecticidal properties, comprising introducing a nucleic acid molecule of the invention as described herein into a plant thereby producing a transgenic plant, wherein the nucleic acid molecule is capable of expressing mCry3A and eCry3.1Ab genes in an amount that results in enhanced insecticidal activity.

The present invention also provides for a method of producing a transgenic plant with enhanced insecticidal properties, comprising the steps of (a) providing a nucleic acid molecule of the invention as described herein; (b) introducing into a plant, tissue culture, or a plant cell the nucleic acid molecule of step (a) to obtain a transformed plant, transformed tissue culture, or a transformed cell comprising enhanced insecticidal properties; and (c) growing said transformed plant or regenerating a transformed plant from the transformed tissue culture or transformed plant cell, so a plant with enhanced insecticidal properties is produced. The present invention also provides for a method of producing transgenic seed from the transgenic plant described above, where the plant is cultured or grown under appropriate conditions to produce progeny seed which is transgenic.

The present invention also provides for a method of producing progeny of any generation of a fertile transgenic plant with enhanced insecticidal properties, comprising the steps of: (a) obtaining an fertile transgenic plant comprising a nucleic acid molecule of the invention as described herein; (b) collecting transgenic seed from said transgenic plant; (c) planting the collected transgenic seed; and (d) growing the progeny transgenic plants from said seed, wherein said progeny has enhanced insecticidal properties relative to a non-transformed plant.

The present invention also provides for a method for producing a plant with enhanced insecticidal properties, comprising the steps of: (a) sexually crossing a first parent plant with a second parent plant, wherein said first or second parent plant is a transgenic plant comprising a nucleic acid molecule of the invention as described herein; and (b) a selecting a first generation progeny plant with enhanced insecticidal properties. In representative embodiments, a method of producing a plant with enhanced insecticidal properties comprises steps (a) and (b) as described above, and optionally (c) selfing the first generation progeny plant, thereby producing a plurality of second generation progeny plants; and (d) selecting from the second generation progeny plants a plant with enhanced insecticidal properties, wherein the second generation progeny plants comprise a nucleic acid molecule of the invention as described herein.

BRIEF DESCRIPTION OF THE DRAWINGS

FIG. 1 is a representation of binary vector 17629, whose nucleic acid sequence is SEQ ID NO: 2.

BRIEF DESCRIPTION OF SEQUENCES IN THE SEQUENCE LISTING

SEQ ID NO: 1 is the nucleic acid sequence of the transgene and comprises expression cassettes comprising mCry3A and eCry3.1Ab coding sequences.

SEQ ID NO: 2 is the nucleic acid sequence of the binary vector 17629.

DETAILED DESCRIPTION OF THE INVENTION

It is to be understood that this invention is not limited to the particular methodology, protocols, cell lines, plant species or genera, constructs, and reagents described herein as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means ±1° C., preferably ±0.5° C. Where the term "about" is used in the context of this invention (e.g., in combinations with temperature or molecular weight values) the exact value (i.e., without "about") is preferred.

The terms "comprises", "comprising", "includes", "including", "having" and their conjugates mean "including but not limited to". The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

"cDNA" refers to a single-stranded or a double-stranded DNA that is complementary to and derived from mRNA. The terms "messenger RNA" or "mRNA" refer to RNA that does not comprise introns and that can be translated into a protein by the cell. The terms "protein," "peptide" and "polypeptide" are used interchangeably herein.

A "control plant" or "control" as used herein may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA.

As used herein, the term "corn" means Zea mays or maize and includes all plant varieties that can be bred with corn, including wild maize species.

To "deliver" or "delivering" a composition or toxin means that the composition or toxin comes in contact with an insect, resulting in a toxic effect and control of the insect. The composition or toxin can be delivered in many recognized ways, e.g., orally by ingestion by the insect via transgenic plant expression, formulated protein composition(s), sprayable protein composition(s), a bait matrix, or any other art-recognized toxin delivery system.

To "control" or "controlling" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

"Effective insect-controlling amount" means that concentration of toxin or toxins that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects. "Insecticidal" is defined as a toxic biological activity capable of controlling insects, preferably by killing them. A transgenic plant with "enhanced insecticidal properties" is a plant that is expresses a protein or proteins at effective insect-controlling amounts, so that, in some embodiments, the plant is insecticidal to an increased range of insect species, relative to a plant of the same kind which is not transformed. This increased range of insect species includes insect plant pests, such as coleopteran insect pests including species of corn rootworm. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm. A transgenic plant with enhanced insecticidal properties may be resistant to corn rootworm infestation.

The term "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The term "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

The term "chimeric construct", "chimeric gene", "chimeric polynucleotide" or chimeric nucleic acid molecule" (and similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains (1) polynucleotides (e.g., DNA), including regulatory and coding polynucleotides that are not found together in nature (i.e., at least one of polynucleotides is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In a preferred aspect of the present invention the chimeric construct, chimeric gene, chimeric polynucleotide or chimeric nucleic acid comprises an expression cassette comprising a polynucleotides of the present invention under the control of regulatory polynucleotides, particularly under the control of regulatory polynucleotides functional in plants.

The term "chromosome" is used herein as recognized in the art as meaning the self-replicating genetic structure in the cellular nucleus containing the cellular DNA and bearing the linear array of genes.

A "coding polynucleotide" is a polynucleotide that is transcribed into RNA, such as mRNA, rRNA, tRNA, snRNA, sense RNA or antisense RNA. Preferably the RNA is then translated in an organism to produce a protein. It may constitute an "uninterrupted coding polynucleotide", i.e., lacking an intron, such as in a cDNA, or it may include one or more introns bounded by appropriate splice junctions. An "intron" is a poly(ribo)nucleotide which is contained in the primary transcript but which is removed through cleavage and religation of the RNA within the cell to create the mature mRNA that can be translated into a protein.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process.

For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

"Expression cassette" as used herein means a nucleic acid molecule capable of directing expression of a particular polynucleotide or polynucleotides in an appropriate host cell, comprising a promoter operably linked to the polynucleotide or polynucleotides of interest which is/are operably linked to termination signals. It also typically comprises polynucleotides required for proper translation of the polynucleotide or polynucleotides of interest. The expression cassette may also comprise polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the particular polynucleotide of the expression cassette does not occur naturally in the host cell and must have been introduced into the host cell or an ancestor of the host cell by a transformation process known in the art. The expression of the polynucleotide(s) in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit consisting of a polynucleotide that occupies a specific location on a chromosome and that contains the genetic instruction for a particular characteristic or trait in an organism, or such hereditary unit from a group of heterologous organisms depending on context.

"Genetic engineering", "transformation" and "genetic modification" are all used herein as synonyms for the transfer of isolated and cloned genes into the DNA, usually the chromosomal DNA or genome, of another organism.

A "transgene" refers to a gene, polynucleotide or nucleic acid introduced into the genome of an organism by genetic manipulation in order to alter its genotype. Transgenes may include, for example, genes, polynucleotides or nucleic acids that are either heterologous or homologous to the particular plant to be transformed. Additionally, transgenes may comprise native genes inserted into a non-native organism, or chimeric genes, polynucleotides or nucleic acids.

The term "genotype" refers to the genetic constitution of a cell or organism. An individual's "genotype for a set of genetic markers" includes the specific alleles, for one or more genetic marker loci, present in the individual. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a sum of one or more alleles present within an individual at one or more genetic loci of a quantitative trait. In some embodiments, a genotype is expressed in terms of a haplotype (defined herein below).

"Transformed," "transgenic," and "recombinant" are used interchangeably and each refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"Wild-type" refers to the normal gene, virus, or organism found in nature without any mutation or modification.

The term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

As used herein, "propagule" refers to any material that is used for propagating a plant, preferably a transgenic plant, more preferably a transgenic plant comprising SEQ ID NO: 1. A propagule may be a seed, cutting, or plurality of cells from a transgenic plant, which can be used to produce a crop of transgenic plants.

As used herein "plant sample" or "biological sample" refers to either intact or non-intact (e.g. milled seed or plant tissue, chopped plant tissue, lyophilized tissue) plant tissue. It may also be an extract comprising intact or non-intact seed or plant tissue. The biological sample or extract may be selected from the group consisting of corn flour, corn meal, corn syrup, corn oil, corn starch, and cereals manufactured in whole or in part to contain corn by-products.

The term "heterologous" when used in reference to a gene or nucleic acid refers to a gene encoding a factor that is not in its natural environment (i.e., has been altered by the hand of man). For example, a heterologous gene may include a gene from one species introduced into another species. A heterologous gene may also include a gene native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, in embodiments, a "heterologous" polynucleotide is a polynucleotide not naturally associated with a host cell into which it is introduced, including non-naturally occurring multiple copies of a naturally occurring polynucleotide.

"Identity" or "percent identity" refers to the degree of similarity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

One example of an algorithm that is suitable for determining percent sequence identity and sequence similarity is the BLAST algorithm, which is described in Altschul et al., J. Mol. Biol. 215: 403 410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873 5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

For DNA-DNA hybrids, the Tm can be approximated from the equation of Meinkoth and Wahl, Anal. Biochem., 138:267-84 (1984): Tm=81.5° C.+16.6 (log M)+0.41 (% GC)−0.61 (% formamide)−500/L; where M is the molarity of monovalent cations, % GC is the percentage of guanosine and cytosine nucleotides in the DNA, % formamide is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired degree of identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, highly stringent conditions can utilize a hybridization and/or wash at the thermal melting point (Tm) or 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). If the desired degree of mismatching results in a Tm of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 3TC and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO4, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

The terms "complementary" or "complementarity" (and similar terms), as used herein, refer to the natural binding of polynucleotides under permissive salt and temperature conditions by base-pairing. For example, the sequence "A-G-T" binds to the complementary sequence "T-C-A." Complementarity between two single-stranded molecules may be partial, in which only some of the nucleotides bind, or it may be complete when total complementarity exists between the single stranded molecules. The degree of complementarity between nucleic acid strands has significant effects on the efficiency and strength of hybridization between the molecules.

As used herein, the term "substantially complementary" (and similar terms) means that two nucleic acid sequences are at least about 50%, 60%, 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein).

The term "isolated", when used in the context of the nucleic acid molecules or polynucleotides of the present invention, refers to a polynucleotide that is identified within and isolated/separated from its chromosomal polynucleotide context within the respective source organism. An isolated nucleic acid or polynucleotide is not a nucleic acid as it occurs in its natural context, if it indeed has a naturally occurring counterpart. In contrast, non-isolated nucleic acids are nucleic acids such as DNA and RNA, which are found in the state they exist in nature. For example, a given polynucleotide (e.g., a gene) is found on the host cell chromosome in proximity to neighboring genes. The isolated nucleic acid molecule may be present in single-stranded or double-stranded form. Alternatively, it may contain both the sense and antisense strands (i.e., the nucleic acid molecule may be double-stranded). In a preferred embodiment, the nucleic acid molecules of the present invention are isolated.

The term "locus" refers to a position (e.g., of a gene, a genetic marker, or the like) on a chromosome of a given species.

The term "linkage", and grammatical variants thereof, refers to the tendency of alleles at different loci on the same chromosome to segregate together more often than would be expected by chance if their transmission were independent, in some embodiments as a consequence of their physical proximity. The phrase "linkage disequilibrium" (also called "allelic association") refers to a phenomenon wherein particular alleles at two or more loci tend to remain together in linkage groups when segregating from parents to offspring with a greater frequency than expected from their individual frequencies in a given population. For example, a genetic marker allele and a QTL allele can show linkage disequilibrium when they occur together with frequencies greater than those predicted from the individual allele frequencies. Linkage disequilibrium can occur for several reasons including, but not limited to the alleles being in close proximity on a chromosome. The term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous to (the physical entity of) chromosome.

The phrase "nucleic acid" or "polynucleotide" refers to any physical string of monomer units that can be corresponded to a string of nucleotides, including a polymer of nucleotides (e.g., a typical DNA polymer or polydeoxyribonucleotide or RNA polymer or polyribonucleotide), modified oligonucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"PCR (polymerase chain reaction)" is understood within the scope of the invention to refer to a method of producing relatively large amounts of specific regions of DNA, thereby making possible various analyses that are based on those regions.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

The term "promoter" refers to a polynucleotide, usually upstream (5') of its coding polynucleotide, which controls the expression of the coding polynucleotide by providing the recognition for RNA polymerase and other factors required for proper transcription. "Constitutive promoter" refers to a promoter that is able to express the open reading frame (ORF) that it controls in all or nearly all of the plant tissues during all or nearly all developmental stages of the plant (referred to as "constitutive expression"). "Regulated promoter" refers to promoters that direct gene expression not constitutively, but in a temporally- and/or spatially-regulated manner, and includes tissue-specific, tissue-preferred and inducible promoters. It includes natural and synthetic polynucleotides as well as polynucleotides which may be a combination of synthetic and natural polynucleotides. Different promoters may direct the expression of a gene in different tissues or cell types, or at different stages of development, or in response to different environmental conditions.

"Tissue-specific promoter" or "tissue-preferred promoter" refers to regulated promoters that are not expressed in all plant cells but only or preferentially in one or more cell types in specific organs (such as leaves or seeds), specific tissues (such as embryo or cotyledon), or specific cell types (such as leaf parenchyma or seed storage cells). These terms also include promoters that are temporally regulated, such as in early or late embryogenesis, during fruit ripening in developing seeds or fruit, in fully differentiated leaf, or at the onset of senescence. Those skilled in the art will understand that tissue-specific promoters need not exhibit an absolute tissue-specificity, but mediate transcriptional activation in most plant parts at a level of about 1% or less of the level reached in the part of the plant in which transcription is most active.

An "enhancer" or "transcriptional enhancer" is a nucleotide sequence that can stimulate promoter activity and can be an innate element of the promoter or a heterologous element inserted to enhance the level or tissue specificity of a promoter. The primary sequence can be present on either strand of a double-stranded DNA molecule, and is capable of functioning even when placed either upstream or downstream from the promoter.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones). Regulatory sequences may be short regions of DNA sequence 6-100 base pairs that define the binding sites for trans-acting factors, such as transcription factors. Regulatory sequences may also be enhancers, longer regions of DNA sequence that can act from a distance from the core promoter region, sometimes over several kilobases from the core region. Regulatory sequence activity may be influenced by trans-acting factors including general transcription machinery, transcription factors and chromatin assembly factors.

"Cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

A "transcriptional terminator" is responsible for the termination of transcription beyond the coding region and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency.

As used herein, gene or trait "stacking" is combining desired genes or traits into one transgenic plant line. As one approach, plant breeders stack transgenic traits by making crosses between parents that each have a desired trait and then identifying offspring that have both of these desired traits (so-called "breeding stacks"). Another way to stack genes is by transferring two or more genes into the cell nucleus of a plant at the same time during transformation. Another way to stack genes is by re-transforming a transgenic plant with another gene of interest. For example, gene stacking can be used to combine two different insect resistance traits, an insect resistance trait and a disease resistance trait, or a herbicide resistance trait (such as, for example, Bt11). The use of a selectable marker in addition to a gene of interest would also be considered gene stacking.

The term "plant" includes reference to whole plants, plant organs, tissues (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

The term "transgenic plant" includes reference to a plant, which comprises within its genome a heterologous nucleic acid sequence. Generally, the heterologous nucleic acid sequence is stably integrated within the genome such that the nucleic acid sequence is passed on to successive generations. The heterologous nucleic acid sequence may be integrated into the genome alone or as part of a recombinant expression cassette. "Transgenic" is used herein to include any cell, cell line, callus, tissue, plant part or plant, the genotype of which has been altered by the presence of a heterologous nucleic acid sequence, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

The term "yield" may include reference to bushels per acre of a grain crop at harvest, as adjusted for grain moisture (15% typically for maize, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art In certain embodiments of the invention yield may be increased in stressed and/or non-stressed conditions.

The term "vector" or "construct" includes reference to a nucleic acid used in transfection of a host cell and into which can be inserted a polynucleotide. Vectors are often replicons. Expression vectors permit transcription of a nucleic acid inserted therein. "Vector" is defined to include, inter alia, any plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

The term "transformation" as used herein refers to the transfer of a nucleic acid fragment into the genome of a host cell, resulting in genetically stable inheritance. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation-sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al 1993, Plant Cell 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen and Willmitzer 1988, Nucleic Acids Res 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Non-transformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as Pseudomonas HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example the maize homeobox gene knl, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107: 193-232; incorporated by reference).

In some embodiments of the invention, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140: 184-195) and a P106S mutation in goosegrass EPSPS (Baerson et al 2002, Plant Physiol 129: 1265-1275). Other sources of EPSPS which are not plant derived and can be used to confer glyphosate tolerance include but are not limited to an EPSPS P101S mutant from *Salmonella typhimurium* (Comai et al 1985, Nature 317: 741-744) and a mutated version of CP4 EPSPS from *Agrobacterium* sp. Strain CP4 (Funke et al 2006, PNAS 103: 13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83: 6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

As used herein, the term transgenic "event" refers to a recombinant plant produced by transformation and regeneration of a plant cell or tissue with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. Typically, transformation of plant tissue produces multiple events, each of which represent insertion of a DNA construct into a different location in the genome of a plant cell. Based on the expression of the transgene or other desirable characteristics, a particular event is selected.

One skilled in the art will recognize that the transgenic genotype of the invention can be introgressed by breeding into other plant lines comprising different transgenic or non-transgenic genotypes. For example, a corn inbred comprising the transgenic genotype of the invention can be crossed with a corn inbred comprising the transgenic genotype of the lepidopteran resistant MIR162 event, which is known in the art, thus producing corn seed that comprises both the transgenic genotype of the invention and the MIR162 transgenic genotype. It will be further recognized that other combinations can be made with the transgenic genotype of the invention and thus this example should not be viewed as limiting.

The transgenic genotype of the invention can be introgressed from the initially transformed plant, such as a corn plant, into an inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

The present invention includes a construct which comprises an mCry3A gene, disclosed in U.S. Pat. No. 7,030,295 (incorporated herein by reference), which encodes an mCry3A protein and is useful in controlling corn rootworm (*Diabrotica* spp.) insect pests. The construct also comprises an eCry3.1Ab gene (also known as FR8a), disclosed in U.S. Pat. No. 8,309,516 and herein incorporated by reference, encoding an eCry3.1Ab insecticidal protein, also useful in controlling *Diabrotica* spp. insect pests via a second mode of action. The dual modes of action conferred by the two insecticidal proteins in a single transgenic corn plant provide growers a more effective management system for the control of corn rootworm.

Although commercial events exist which carry either the mCry3A gene (namely event MIR604, U.S. Pat. Nos. 7,361,813, 7,897,748, 8,354,519, and 8,884,102) or the eCry3.1Ab gene (namely event 5307, U.S. Pat. No. 8,466,346), a single event which carries both genes at a single locus would provide significant advantages. Currently, the creation of a commercially useful transgenic plant that comprises both mCry3A and eCry3.1Ab transgenes requires multiple breeding steps and a significant amount of screening to identify the correct genotype in the correct germplasm. These breeding and screening steps are required for every variety of germplasm into which introduction of these two traits is desirable. Additionally, for many agronomically important crops, such as corn, these two traits need to be maintained as hybrids for dozens of germplasm varieties. Finally, factors such as the genetic linkage of undesirable traits or genetic recombination may complicate the introduction of two traits from two distinct loci into a single germplasm variety. Therefore, it would be advantageous to create a nucleic acid molecule which, when introduced into the genome of a cell, will result in a transgenic cell that carries both traits at a single locus.

Different constructs were produced to determine the efficacy of the mCry3A and eCry3.1Ab genes in the context of different expression cassettes. Surprisingly, one vector, 17629, conferred excellent insecticidal properties with no or minimal negative effects on the vegetative development or the fertility of the transgenic plant. The transgene from vector 17629 is SEQ ID NO: 1. This transgene comprises three expression cassettes. Two of those expression cassettes comprise eCry3.1Ab and mCry3A, which are genes that are useful in controlling coleopteran insect pests, including *Diabrotica virgifera virgifera*, the western corn rootworm, *D. virgifera zeae*, the Mexican corn rootworm, and *D. longicornis barberi*, the northern corn rootworm. The third expression cassette comprises the PAT gene, which confers resistance to herbicides containing glufosinate. The PAT gene is derived from *Streptomyces viridochromogenes* and encodes a phosphinothricin acetyltransferase which confers tolerance to glufosinate. (U.S. Pat. Nos. 5,531,236, 5,646, 024, 5,648,477, and 5,276,268). The PAT gene can be used as a selectable marker for transformation. Transgenic plants expressing the PAT gene also have tolerance to herbicides containing glufosinate. Therefore, a transgenic plant comprising SEQ ID NO: 1 has both enhanced insecticidal properties and herbicide tolerance.

A skilled person would recognize that during the insertion of a nucleic acid molecule, such as SEQ ID NO: 1, into a cell, the 5' and/or 3' ends of the inserted molecule may be deleted or rearranged. Such deletions or rearrangements may not affect the function of the inserted molecule, and these relatively small changes result in an inserted molecule that may be considered to be substantially identical to SEQ ID NO: 1. A skilled person would also recognize that the nucleic acid molecule, such as one comprising SEQ ID NO: 1, may undergo full or partial rearrangement or duplication during the insertion event, such that the inserted molecule is a full or partial rearrangement or duplication of the starting nucleic acid molecule. A skilled person would recognize that this inserted molecule may still have the same characteristics and/or traits as the starting molecule, such that the inserted molecule is substantially identical to SEQ ID NO: 1, and the transformed cell or resulting transformed plant may still be desirable.

A skilled person would recognize that a transgene for commercial use, such as a nucleic acid molecule that comprises SEQ ID NO: 1, may need relatively minor modifications to the nucleic acid sequence to comply with governmental regulatory standards. Such modifications would not affect the function of the resulting molecule, which would be substantially identical to SEQ ID NO: 1. A skilled person would recognize that the modified nucleic acid molecule would be essentially the same as the starting molecule.

Therefore, the invention encompasses a nucleic acid molecule substantially identical to SEQ ID NO: 1, wherein certain nucleotides of SEQ ID NO: 1 are deleted, substituted or rearranged, resulting in a mutated SEQ ID NO:1 and wherein the functionality of the mutated SEQ ID NO:1 is the same as the starting molecule. The present invention also provides for a nucleic acid molecule, a chimeric nucleic acid molecule, and/or a recombinant nucleic acid construct or vector which comprise, consist, or essentially consist of a nucleic acid sequence that is at least 90% identical, at least 95% identical, at least 97% identical, at least 98% identical, at least 99% identical, or 100% identical to SEQ ID NO: 1. In one embodiment, this chimeric nucleic acid molecule may comprise additional expression cassettes, transcriptional or translational regulatory elements, or prokaryotic origins of replication. In another embodiment, the chimeric nucleic acid molecule may be a recombinant nucleic acid construct, such as a binary vector or a vector suitable for expression in prokaryotes. The recombinant nucleic acid construct may be suitable for transient or stable expression in plants. In one embodiment, a nucleic acid molecule of the invention as described herein is an isolated nucleic acid molecule. In another embodiment, the invention encompasses SEQ ID NO: 1 or a nucleic acid molecule that is substantially identical to SEQ ID NO: 1as either an isolated nucleic acid molecule or as part of a larger nucleic acid molecule.

In another embodiment, the present invention encompasses the use of SEQ ID NO: 1 or a nucleic acid molecule that is substantially identical to SEQ ID NO: 1, wherein expression of said molecule confers enhanced insecticidal properties useful in controlling coleopteran insect pests including *Diabrotica virgifera virgifera*, the western corn rootworm, *D. virgifera zeae*, the Mexican corn rootworm, and *D. longicornis barberi*, the northern corn rootworm.

In another embodiment, the present invention encompasses a transgenic host cell comprising a nucleic acid molecule comprising SEQ ID NO: 1 or a nucleic acid molecule that is substantially identical to SEQ ID NO: 1. In some embodiments, the cell may be a bacterial cell or a plant cell. In some embodiments, the bacterial cell may be an *Escherichia coli, Bacillus thuringiensis, Bacillus subtilis, Bacillus megaterium; Bacillus cereus, Agrobacterium* ssp. or a *Pseudomonas* ssp. cell.

In another embodiment, the present invention encompasses a transgenic plant, plant part, plant tissue, plant cell culture, or plant cell comprising a transgenic plant cell comprising a nucleic acid molecule comprising SEQ ID NO: 1 or a nucleic acid molecule that is substantially identical to SEQ ID NO: 1. In some embodiments, this nucleic acid molecule may be a chromosome, into which a nucleic acid molecule of the invention as described herein has integrated. The transgenic plant cell may or may not be capable of regenerating into a transgenic plant. The transgenic plant may be a monocot plant or a dicot plant. In some embodiments, the transgenic plant may be a crop plant, including but not limited to maize, sorghum, wheat, sunflower, tomato, crucifers, oat, turf grass, pasture grass, peppers, potato, cotton, rice, soybean, sugarcane, sugar beet, tobacco, barley, or oilseed rape.

In another embodiment, the present invention encompasses a progeny of any generation of the transgenic plant, wherein the progeny comprises SEQ ID NO: 1 or a nucleic acid molecule that is substantially identical to SEQ ID NO: 1. In another embodiment, the invention encompasses a propagule from any generation of the transgenic plant, wherein the propagule comprises SEQ ID NO: 1 or a nucleic acid molecule that is substantially identical to SEQ ID NO: 1. In some embodiments, the propagule may be a seed or a cutting. The cutting may be from a part of the transgenic plant that is above ground, such as a stem or a leaf, or underground, such as a root or rhizome.

In another embodiment, the present invention encompasses a method of producing a transgenic plant with enhanced insecticidal properties, comprising introducing SEQ ID NO: 1 or a nucleic acid molecule that is substantially identical to SEQ ID NO: 1 into a plant thereby producing a transgenic plant, wherein the nucleic acid molecule causes the expression of the mCry3A and eCry3.1 Ab genes in an amount that provides insect control. In one embodiment, the nucleic acid molecule may be introduced into the plant by a method of transformation, including but not limited to *Agrobacterium*-mediated transformation or biolistic or particle bombardment. Such a method would include the steps of a) providing the nucleic acid molecule; b) introducing into a plant, tissue culture, or a plant cell the nucleic acid molecule of step (a) to obtain a transformed plant, transformed tissue culture, or a transformed cell having enhanced insecticidal properties; and c) growing said transformed plant or regenerating a transformed plant from the transformed tissue culture or transformed plant cell, so a transgenic plant with enhanced insecticidal properties is produced.

In another embodiment, the nucleic acid molecule also may be introduced into a plant by breeding, including selfing or outcrossing, such that the progeny carries the nucleic acid molecule. In one embodiment, the method would include the steps of a) obtaining a fertile transgenic plant comprising a nucleic acid molecule comprising SEQ ID NO: 1 or a nucleic acid molecule that is substantially identical to SEQ ID NO: 1; b) growing said plant under appropriate conditions to produce said transgenic seed. In another embodiment, the method would include the steps of a) obtaining a fertile transgenic plant comprising a nucleic acid molecule comprising SEQ ID NO: 1 or a nucleic acid molecule that is substantially identical to SEQ ID NO: 1; b) sexually crossing the transgenic parent plant with a second parent plant; c) selecting a first generation progeny plant with enhanced insecticidal properties. Optionally, a method may include further steps of d) selfing the first generation progeny plant, thereby producing a plurality of second generation progeny plants; and e) selecting from the second generation progeny plants a plant with enhanced insecticidal properties, wherein the second generation progeny plants comprise a nucleic acid molecule comprising SEQ ID NO: 1 or a nucleic acid molecule that is substantially identical to SEQ ID NO: 1 and the second generation progeny plants have enhanced insecticidal properties relative to a non-transgenic plant.

EXAMPLES

Example 1: Constructs Synthesized

Five binary vector constructs were constructed with differing combinations of transcriptional enhancers, promoters, translational enhancers, and terminators, and variants of these genetic elements, driving expression of variants of mCry3A and eCry3.1Ab. All promoters used are known to be strong constitutive promoters, and the addition of the transcriptional and translational enhancers were expected to result in transgenic plants with excellent levels of expression and insect control. Versions of mCry3A and eCry3.1Ab genes were created with differing codon preferences, to reduce nucleotide sequence identity between the two. Regions of nucleotide sequence identity between the mCry3A and eCry3.1Ab genes could result in a reduction of gene expression, at the transcriptional or post-transcriptional level. Therefore, designing nucleotide sequences with minimal identity may result in higher expression of either or both mCry3A and eCry3.1Ab genes in a transgenic plant. Table 1 shows the five constructs created, and lists the genetic elements with each coding sequence (CDS). Table 2 describes each of the genetic elements named in Table 1.

TABLE 1

Composition of Binary Constructs

| Construct ID | Cassette position | Transcriptional Enhancer | Promoter | CDS | Terminator |
|---|---|---|---|---|---|
| 17629 | 1 | eNOS-02 | prCMP-04 | eCry3.1Ab-01 | tNOS-05-01 |
|  | 2 |  | prUbi1-18 | mCry3A-01 | tNOS-20 |
|  | 3 |  | pr35S-04 | cPAT-08 | tNOS-05-01 |
| 18382 | 1 | eNOS-02 | prCMP-09 | eCry3.1Ab-03 | tZmUbi158-01 |
|  | 2 |  | prUbi1-18 | mCry3A-04 | tZmUbi361-01 |
|  | 3 |  | pr35S-19 | cPAT-09 | tNOS-05-01 |
| 21371 | 1 | eNOS-03 | prCMP-15 | eCry3.1Ab-04 | tNOS-25 |
|  | 2 |  | prUbi1-38 | mCry3A-05 | tNOS-25 |
|  | 3 |  | pr35S-19 | cPAT-09 | tNOS-05-01 |
| 21629 | 1 | eNOS-02 | prCMP-04 | eCry3.1Ab-01 | tNOS-05-01 |
|  | 2 |  | prUbi1-38 | mCry3A-05 | tUbi1-05 |
|  | 3 |  | pr35S-19 | cPAT-09 | tNOS-05-01 |
| 21630 | 1 | eNOS-02 | prCMP-04 | eCry3.1Ab-01 | tNOS-05-01 |
|  | 2 |  | prSoUbi4-01 | mCry3A-05 | t35S-09 |
|  | 3 |  | pr35S-19 | cPAT-09 | tNOS-05-01 |
| 21386 | 1 | eNOS-03 | prCMP-15 | eCry3.1Ab-04 | tNOS-25 |
|  | 2 | eFMV-06:e35S-11 | prUbi1-38 | mCry3A-05 | tNOS-25 |
|  | 3 |  | pr35S-19 | cPAT-09 | tNOS-05-01 |
| 21648 | 1 | eNOS-02 | prCMP-04 | eCry3.1Ab-05 | tNOS-05-01 |
|  | 2 |  | prUbi1-38 | mCry3A-05 | tUbi1-05 |
|  | 3 |  | pr35S-19 | cPAT-09 | tNOS-05-01 |
| 21649 | 1 | eNOS-02 | prCMP-04 | eCry3.1Ab-05 | tNOS-05-01 |
|  | 2 |  | prSoUbi4-01 | mCry3A-05 | t35S-09 |
|  | 3 |  | pr35S-19 | cPAT-09 | tNOS-05-01 |

TABLE 2

Description of Genetic Elements

| Element | Name | Description |
|---|---|---|
| transcriptional enhancer | eNOS-02 | Modified NOS enhancer from *Agrobacterium tumefaciens* |
| transcriptional enhancer | eFMV-06 | Modified figwort mosaic virus enhancer region (similar to NCBI accession number X06166.1; Maiti et al. 1997, *Transgenic Res* 6: 143-156). Differs from eFMV-03 by 3 bp changes. |
| transcriptional enhancer | e35S-11 | Cauliflower mosaic virus 35S enhancer region which can activate heterologous core promoters (Ow etal. 1987, PNAS 84: 4870-4874.) Differs from e35S-05 by 2 bp changes. |
| promoter | pr35S-04 | Modified promoter region of cauliflower mosaic virus (Odell et al. 1985, *Nature* 313: 810-812). |
| promoter | pr35S-19 | Differs from pr35S-04 by 4 nucleotide changes. |
| promoter | prCMP-04 | Cestrum yellow leaf curling virus promoter region (Hohn et al. 2007; U.S. Pat. No. 7,166,770). Provides constitutive expression in maize. |
| promoter | prCMP-09 | Differs from prCMP-04 by 3 nucleotide changes |
| promoter | prCMP-15 | Differs from prCMP-04 by 5 nucleotide changes |
| promoter | prUbi1-18 | Modified maize ubiquitin promoter, similar to the maize polyubiquitin promoter NCBI accession number S944646.1; (Christensen et al. 1992, PMB 18: 675-689). |
| promoter | prUbi1-38 | Differs from prUbi1-18 by 8 nucleotide changes |
| promoter | prSoUbi4-01 | Sugarcane ubiquitin promoter, similar to the sugarcane tetra-ubiquitin (ubi4) gene, GenBank accession number AF093504, U.S. Pat. No. 6,706,948. |
| coding sequence | eCry3.1Ab-01 | An engineered Cry gene active against certain corn rootworm (Diabrotica) species. U.S. Pat. No. 8,309,516. |
| coding sequence | eCry3.1Ab-03 | This version of eCry3.1Ab is based on eCry3.1Ab-01 and has the same amino acid sequence, however the codon preference was changed to reduce usage of most frequently used codons and to reduce nucleotide sequence identity with mCry3A and Cry1Ab. The nucleotide sequence was also optimized for commercial usage and to comply with governmental regulatory standards. |
| coding sequence | eCry3.1Ab-04 | This version of eCry3.1Ab is based on eCry3.1Ab-01 and has the same amino acid sequence, however the codon preference was changed, using a strategy different from that of eCry3.1Ab-03, to reduce usage of most frequently used codons and to reduce nucleotide sequence identity with mCry3A and Cry1Ab. The nucleotide sequence was also optimized for commercial usage and to comply with governmental regulatory standards. |
| coding sequence | eCry3.1Ab-05 | This version of eCry3.1Ab is based on eCry3.1Ab-01 and has the same amino acid sequence, except for a S153T mutation. The codon preference was changed, using a strategy different from that of eCry3.1Ab-03 or eCry3.1Ab-04, to reduce usage of most frequently used codons and to reduce sequence identity with mCry3A and Cry1Ab. The nucleotide sequence was also optimized for commercial usage and to comply with governmental regulatory standards. |
| coding sequence | mCry3A-01 | A maize-optimized cry3A based on the native Cry3A protein sequence from *B. thuringiensis* subsp. *tenebrionis* (Sekar et al. 1987, PNAS 84: 7036-7040; U.S. Pat. Nos. 7,030,295 and 7,276,583) |
| coding sequence | mCry3A-04 | This version of mCry3A is based on mCry3A-01 and has the same amino acid sequence. The nucleotide sequence was optimized for commercial usage and to comply with governmental regulatory standards. |
| coding sequence | mCry3A-05 | This version of mCry3A is based on mCry3A-01 and has the same amino acid sequence, however the codon preference was changed to reduce usage of most frequently used codons and to reduce nucleotide sequence identity with eCry3.1Ab. The nucleotide sequence was also optimized for commercial usage and to comply with governmental regulatory standards. |
| coding sequence | cPAT-08 | A modified version of the *Streptomyces viridochromogenes* strain Tu494 gene encoding the selectable marker PAT. The native coding sequence (Wohlleben et al. 1988, Gene 70: 25-37) was codon-optimized for enhanced expression. PAT confers resistance to herbicides containing glufosinate (phosphinothricin. (U.S. Pat. Nos. 5,531,236, 5,646,024, 5,648,477, and 5,276,268). |
| coding sequence | cPAT-09 | Differs from cPAT-08 by 6 nucleotide changes; has the same amino acid sequence. |
| terminator | tNOS-05-01 | Terminator sequence based on the NOS gene of *A. tumefaciens* (NCBI accession number V00087.1). Provides a polyadenylation site (Bevan etal. 1983, *Nucleic Acids Res* 11: 369-385) |

TABLE 2-continued

Description of Genetic Elements

| Element | Name | Description |
|---|---|---|
| terminator | tNOS-20 | Modified terminator sequence based on the NOS gene of *A. tumefaciens* (NCBI accession number V00087.1). Provides a polyadenylation site (Bevan et al. 1983). |
| terminator | tNOS-25 | Differs from tNOS-05-01 by one nucleotide change. |
| terminator | tZmUbi158-01 | Terminator sequence based on the maize Ubiquitin ZmU29158-3 gene. U.S. Patent Application No. 13/377,170. |
| terminator | tZmUbi361-01 | Terminator sequence based on maize Ubiquitin ZM066361 gene. U.S. Patent Application No. 13/377,170. |
| terminator | tUbi1-05 | Terminator sequence based on *Zea mays* Ubi1 gene. The nucleotide sequence was optimized for commercial usage and to comply with governmental regulatory standards. |
| terminator | t35S-09 | Modified Cauliflower Mosaic Virus 35S terminator (Genbank V00141 J02048) |

Example 2: Transformation in Corn Plants

Each of the eight binary vector constructs was used to create maize transgenic events. Events were produced by *Agrobacterium*-mediated transformation of a proprietary maize line. Immature embryos were transformed essentially as described in Negrotto et al. (2000, *Plant Cell Reports* 19: 798-803). Using this method, genetic elements within the left and right border regions of the transformation plasmid were efficiently transferred and integrated into the genome of the plant cell, while genetic elements outside these border regions were not transferred.

The PAT gene was used as a selectable marker during the transformation process (Negrotto et al. 2000). The embryos producing embryogenic calli were transferred to a series of cell culture selection media containing bialaphos as selection agent and cultured for 10-11 weeks in total. The selection media contained 200 mg/ml timentin and/or 10 ml/l PPM (Plant Preservative Mix) to ensure that the *Agrobacterium* was cleared from the transformed tissue.

Regenerated plantlets were tested for the presence of the PAT gene and other target genes by real-time TAQMAN® PCR analysis developed by Ingham et al. (Biotechniques 31(1):132-4, 136-40, 2001). Plants positive for PAT and target genes, also referred to as events, were transferred to the greenhouse for further propagation.

Example 3: Gene Expression Determined by Quantitative Sandwich ELISA

To determine the expression levels of mCry3a and eCry3.1Ab, quantitative ELISA was performed using a duplex method to measure the amounts of mCry3a and eCry3.1Ab proteins in the same sample at the same time. Samples were taken from the roots of transgenic events and extracted in phosphate buffered saline pH 7.3 (PBS) containing 0.05% Tween-20 (PBST). Total soluble protein (TSP) of the extract was measured using the Pierce BCA Protein Assay (Thermo Scientific, Rockford, Ill.). High-binding 96-well plates (Nunc Maxisorp) were coated with 2 µg/ml MAb170 anti-mCry3A in buffer. Plates were washed three times with phosphate buffered saline pH 7.3 (PBS) containing 0.05% Tween-20 (PBST). Samples or standards in ELISA diluent (PBST containing 1% bovine serum albumin) were added to the plate (100 µl/well), incubated for 1 hr at room temperature (RT) with shaking, and washed five times. 100 µl/well of 0.5 ug/mL HRP-rabbit anti-Cry1Ab, 1 µg/mL Biotin-MAb174 anti-mCry3A, and 0.1 µg/mL Streptavidin-AP (Jackson ImmunoResearch Labs, West Grove, Pa.) in ELISA diluent was added to the plate, incubated for 1 hr at RT/shaking, and washed as before. Substrate p-nitrophenyl phosphate (SurModics, Eden Prairie, Minn.) was added (100 µl/well) and allowed to develop for 30 min at room temperature. The absorbance was measured at 405 nm using a microplate reader (BioTek Powerwave XS2, Winooski, Vt.) for measuring mCry3A. The plate was washed as before. Substrate Tetramethylbenzidine (Sigma, St. Louis, Mo.) was added (100 µl/well) and allowed to develop for 30 min at room temperature with shaking. The reaction was stopped using 1 N HCl (100 µl/well). The absorbance was measured at 450 nm for detecting eCry3.1Ab. To normalize for extraction efficiency, the concentration of the analyte (mCry3A or eCry3.1Ab) was divided by the concentration of the total soluble protein (TSP). The standard curve used a four-parameter curve fit to plot the concentrations versus the absorbance.

TABLE 3

Summary of mCry3A expression data

| Construct ID | # of events | ng mCry3A/mg TSP (average) |
|---|---|---|
| 17629 | 137 | 225 |
| 18382 | 20 | 628 |
| 21371 | 103 | 76 |
| 21629 | 181 | 38 |
| 21630 | 158 | 20 |
| 21386 | 42 | 46 |
| 21648 | 45 | 44 |
| 21649 | 197 | 80 |

Protein accumulation of mCry3A was highest, on average, in the events generated from transformation of binary construct 18382. Transgenic plants generated from transformation of binary constructs 21371, 21629, 21630, 21386, 21648, and 21649 had poor efficacy against western corn rootworm due to low protein levels.

TABLE 4

Summary of eCry3.1Ab expression data

| Construct ID | # of events | ng eCry3.1Ab/mg TSP (average) |
|---|---|---|
| 17629 | 137 | 1177 |
| 18382 | 20 | 139 |
| 21371 | 103 | 47 |
| 21629 | 181 | 194 |
| 21630 | 158 | 223 |

TABLE 4-continued

Summary of eCry3.1Ab expression data

| Construct ID | # of events | ng eCry3.1Ab/mg TSP (average) |
|---|---|---|
| 21386 | 42 | 0 |
| 21648 | 45 | 204 |
| 21649 | 197 | 85 |

Protein amounts of eCry3.1Ab were the highest, on average, in the events generated from transformation of binary construct 17629. Surprisingly, events generated from the remaining constructs had much lower amounts of eCry3.1Ab protein.

Example 4: Efficacy Trials for Events Comprising 17629 and 18382 Transgenes 49 transgenic corn events comprising the transgene from 17629 and 12 transgenic events comprising the transgene from 18382 were evaluated for Western Corn Rootworm field efficacy in two different hybrids (hybrids A and B) at a total of 8 different locations in the United States. Events were planted in three row plots with 3 replications each. Four inch root feeding damage ratings were made on 6 plants from the center row. For hybrid A, 21 of 49 events comprising the transgene from 17629 and 12 of 12 events comprising the transgene from 18382 had acceptable efficacy against Western Corn Rootworm, with a 5% confidence level. For hybrid B, 31 of 49 events comprising the transgene from 17629 and 12 of 12 events comprising the transgene from 18382 had acceptable efficacy against Western Corn Rootworm.

Example 5: Agronomic Equivalence Trials for Events Comprising 17629 and 18382 Transgenes 49 transgenic corn events comprising the transgene from 17629 and 12 transgenic events comprising the transgene from 18382 were evaluated for Western Corn Rootworm field efficacy in two different hybrids (hybrids A and B) at a total of 16 different locations in the United States. Events were planted in two row plots with 3 replications each. Grain yield was measured as bushels per acre, and a Least Squares Mean Analysis was performed. For hybrid A, all events comprising the transgene from 17629 performed at least as well as the control check, which was a transgenic plant comprising the same eCry3.1Ab transgene as event 5307. However, for hybrid A, 8 of 11 events comprising the transgene from 18382 performed significantly worse than the control check. For hybrid B, all events comprising the transgene from 17629 performed at least as well as the control check. For hybrid B, 1 of 11 events comprising the transgene from 18382 performed significantly worse than the control check. Surprisingly, despite the excellent levels of mCry3A and eCry3.1Ab protein (as shown in Tables 3 and 4) and the excellent field efficacy as described in Example 4 of events generated using vector 18382, only the events generated using vector 17629 had both good efficacy and good performance. Therefore, only vector 17629 satisfied all the requirements for generating high performing transgenic maize events.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A nucleic acid molecule comprising a nucleic acid sequence that is at least 98% identical to SEQ ID NO: 1 and encodes mCry3A and eCry3.1Ab insecticidal proteins, or the complement thereof.

2. An isolated nucleic acid molecule comprising a nucleic acid sequence that is at least 98% identical to SEQ ID NO: 1 and encodes mCry3A and eCry3.1Ab insecticidal proteins, or the complement thereof.

3. A chimeric nucleic acid molecule comprising the nucleic acid molecule of claim 1.

4. A recombinant nucleic acid vector comprising the nucleic acid molecule of claim 1.

5. A transgenic host cell comprising the nucleic acid molecule of claim 1.

6. A transgenic host cell according to claim 5, wherein said cell is a bacterial cell or a plant cell.

7. The host cell according to claim 6, wherein said cell is an *Escherichia coli*, *Bacillus thuringiensis*, *Bacillus subtilis*, *Bacillus megaterium*, *Bacillus cereus*, *Agrobacterium* ssp. or a *Pseudomonas* ssp. cell.

8. A transgenic plant, plant part, plant tissue, or plant cell culture comprising the transgenic plant cell of claim 6.

9. The transgenic plant according to claim 8, wherein said plant is a monocot plant.

10. The transgenic plant according to claim 8, wherein said plant is a dicot plant.

11. A transgenic plant according to claim 8, wherein said plant is selected from the group consisting of maize, sorghum, wheat, sunflower, tomato, crucifers, oat, turf grass, pasture grass, peppers, potato, cotton, rice, soybean, sugarcane, sugar beet, tobacco, barley, and oilseed rape.

12. A progeny of any generation of the plant of claim 8, wherein the progeny comprises a nucleic acid sequence that is at least 98% identical to SEQ ID NO: 1 and encodes mCry3A and eCry3.1Ab insecticidal proteins, or the complement thereof.

13. A propagule from any generation of the transgenic plant of claim 8, wherein the propagule comprises a nucleic acid sequence that is at least 98% identical to SEQ ID NO: 1 and encodes mCry3A and eCry3.1Ab insecticidal proteins, or the complement thereof.

14. The propagule of claim 13, further defined as a seed or a cutting.

15. A method of producing a transgenic plant with enhanced insecticidal properties, comprising introducing the nucleic acid molecule of claim 1 into a plant thereby producing a transgenic plant, wherein the nucleic acid molecule expresses effective insect-controlling amounts of protein.

16. A method of producing a transgenic plant with enhanced insecticidal properties, comprising the steps of:
   a) providing the nucleic acid molecule of claim 1;
   b) introducing into a plant, tissue culture, or a plant cell the nucleic acid molecule of step (a) to obtain a transformed plant, transformed tissue culture, or a transformed cell having enhanced insecticidal properties; and
   c) growing said transformed plant or regenerating a transformed plant from the transformed tissue culture or transformed plant cell, so a transgenic plant with enhanced insecticidal properties is produced.

17. A method of producing transgenic seed, comprising the steps of:
   a) obtaining a fertile transgenic plant according to claim 8; and
   b) growing said plant under appropriate conditions to produce said transgenic seed.

18. A method of producing progeny of any generation of a fertile transgenic plant with enhanced insecticidal properties, comprising the steps of:
   a) obtaining a fertile transgenic plant with enhanced insecticidal properties comprising the nucleic acid molecule of claim 1;
   b) collecting transgenic seed from said transgenic plant;
   c) planting the collected transgenic seed; and
   d) growing the progeny transgenic plants from said seed, wherein said progeny has enhanced insecticidal properties relative to a non-transformed plant.

19. A method for producing a transgenic plant with enhanced insecticidal properties, comprising the steps of sexually crossing a first parent plant with a second parent plant, wherein said first or second parent plant is the plant of claim 8, to produce a first generation progeny plant that comprises a nucleic acid sequence that is at least 98% identical to SEQ ID NO: 1 and encodes mCry3A and eCry3.1Ab insecticidal proteins, or the complement thereof.

20. A method for producing a transgenic plant with enhanced insecticidal properties, comprising the steps of:
   a) sexually crossing a first parent plant with a second parent plant, wherein said first or second parent plant is the plant of claim 8; and
   b) selecting a first generation progeny plant with enhanced insecticidal properties, wherein the selected progeny plant comprises a nucleic acid sequence that is at least 98% identical to SEQ ID NO: 1 and encodes mCry3A and eCry3.1Ab insecticidal proteins, or the complement thereof.

21. The method of claim 20, further comprising the steps of:
   a) selfing the first generation progeny plant, thereby producing a plurality of second generation progeny plants; and
   b) selecting from the second generation progeny plants a plant with enhanced insecticidal properties, wherein the selected second generation progeny plants comprise a nucleic acid sequence that is at least 98% identical to SEQ ID NO: 1 and encodes mCry3A and eCry3.1Ab insecticidal proteins, or the complement thereof.

22. The nucleic acid molecule of claim 1, wherein the nucleic acid sequence comprises SEQ ID NO: 1, or the complement thereof.

\* \* \* \* \*

SEQUENCE LISTING

```
<160> NUMBER OF SEQ ID NOS: 2

<210> SEQ ID NO 1
<211> LENGTH: 8295
<212> TYPE: DNA
<213> ORGANISM: Artificial Sequence
<220> FEATURE:
<223> OTHER INFORMATION: Source organisms include Cestrum Yellows Leaf
      Curl Virus, Bacillus thuringiensis, Agrobacterium tumefaciens, Zea
      mays, and Cauliflower Mosaic Virus

<400> SEQUENCE: 1
tcattgagcg gagaattaag ggagtcacgt tatgaccccc gccgatgacg cgggacaagc      60
cgttttacgt ttggaactga cagaaccgca acgaatattg gcagacaaag tggcagacat     120
actgtcccac aaatgaagat ggaatctgta aaagaaaacg cgtgaaataa tgcgtctgac     180
aaaggttagg tcggctgcct ttaatcaata ccaaagtggt ccctaccacg atggaaaaac     240
tgtgcagtcg gtttggcttt ttctgacgaa caaataagat tcgtggccga caggtggggg     300
tccaccatgt gaaggcatct tcagactcca ataatggagc aatgacgtaa gggcttacga     360
aataagtaag ggtagtttgg gaaatgtcca ctcacccgtc agtctataaa tacttagccc     420
ctccctcatt gttaagggag caaaatctca gagagatagt cctagagaga gaaagagagc     480
aagtagccta gaagtggatc caccatgact agtaacggcc gccagtgtgc tggtattcgc     540
```

```
ccttatgacg gccgacaaca acaccgaggc ctggacagca gcaccaccaa ggacgtgatc    600
cagaagggca tcagcgtggt gggcgacctg ctgggcgtgg tgggcttccc cttcggcggc    660
gccctggtga gcttctacac caacttcctg aacaccatct ggcccagcga ggacccctgg    720
aaggccttca tggagcaggt ggaggccctg atggaccaga gatcgccga ctacgccaag     780 aacaaggcac tggccgagct acagggcctc cagaacaacg tggaggacta tgtgagcgcc    840
ctgagcagct ggcagaagaa ccccgctgca ccgttccgca accccacag ccagggccgc     900 atccgcgagc tgttcagcca ggccgagagc cacttccgca acagcatgcc cagcttcgcc    960
atcagcggct acgaggtgct gttcctgacc acctacgccc aggccgccaa cacccacctg    1020
ttcctgctga aggacgccca atctacgga gaggagtggg gctacgagaa ggaggacatc     1080
gccgagttct acaagcgcca gctgaagctg acccaggagt acaccgacca ctgcgtgaag    1140
tggtacaacg tgggtctaga caagctccgc ggcagcagct acgagagctg ggtgaacttc    1200
aaccgctacc gccgcgagat gaccctgacc gtgctggacc tgatcgccct gttcccctg     1260 tacgacgtgc gcctgtaccc caaggaggtg aagaccgagc tgacccgcga cgtgctgacc    1320
gaccccatcg tgggcgtgaa caacctgcgc ggctacggca ccaccttcag caacatcgag    1380
aactacatcc gcaagcccca cctgttcgac tacctgcacc gcatccagtt ccacacgcgt    1440
ttccagcccg gctactacgg caacgacagc ttcaactact ggagcggcaa ctacgtgagc    1500
acccgcccca gcatcggcag caacgacatc atcaccagcc ccttctacgg caacaagagc    1560
agcgagcccg tgcagaacct tgagttcaac ggcgagaagg tgtaccgcgc cgtggctaac    1620
accaacctgg ccgtgtggcc ctctgcagtg tacagcggcg tgaccaaggt ggagttcagc    1680
cagtacaacg accagaccga cgaggccagc acccagacct acgacagcaa gcgcaacgtg    1740
ggcgccgtga gctgggacag catcgaccag ctgcccccg agaccaccga cgagcccctg     1800
gagaagggct acagccacca gctgaactac gtgatgtgct tcctgatgca gggcagccgc    1860
ggcaccatcc ccgtgctgac ctggaccac aagagcgtcg acttcttcaa catgatcgac    1920
agcaagaaga tcacccagct gccccctgacc aagagcacca acctgggcag cggcaccagc    1980
gtggtgaagg ccccggcttc accggcggc gacatcctgc ccgcaccag ccccggccag     2040 atcagcaccc tgcgcgtgaa catcaccgcc cccctgagcc agcgctaccg cgtccgcatc    2100
cgctacgcca gcaccaccaa cctgcagttc cacaccagca tcgacggccg ccccatcaac    2160
cagggcaact tcagcgccac catgagcagc ggcagcaacc tgcagagcgg cagcttccgc    2220
accgtgggct tcaccacccc cttcaacttc agcaacggca gcagcgtgtt caccctgagc    2280
gcccacgtgt tcaacagcgg caacgaggtg tacatcgacc gcatcgagtt cgtgcccgcc    2340
gaggtgacct tcgaggccga gtacgacctg gagagggctc agaaggccgt gaacgagctg    2400
ttcaccagca gcaaccagat cggcctgaag accgacgtga ccgactacca catcgatcag    2460
gtgtaggagc tgagctcttc atatgacgat cgttcaaaca tttggcaata agtttcttta    2520
agattgaatc ctgttgccgg tcttgcgatg attatcatat aatttctgtt gaattacgtt    2580
aagcatgtaa taattaacat gtaatgcatg acgttattta tgagatgggt ttttatgatt    2640
agagtcccgc aattatacat ttaatacgcg atagaaaaca aaatatagcg cgcaaactag    2700
gataaattat cgcgcgcggt gtcatctatg ttactagatc gcggacccaa gcttgcatgc    2760
ctgcagtgca gcgtgacccg gtcgtgcccc tctctagaga taatgagcat tgcatgtcta    2820
agttataaaa aattaccaca tatttttttt gtcacacttg tttgaagtgc agtttatcta    2880
```

```
tctttataca tatatttaaa ctttactcta cgaataatat aatctatagt actacaataa      2940
tatcagtgtt ttagagaatc atataaatga acagttagac atggtctaaa ggacaattga      3000
gtattttgac aacaggactc tacagtttta tcttttagt gtgcatgtgt tctccttttt       3060
ttttgcaaat agcttcacct atataatact tcatccattt tattagtaca tccatttagg      3120
gtttagggtt aatggttttt atagactaat ttttttagta catctatttt attctatttt      3180
agcctctaaa ttaagaaaac taaaactcta ttttagtttt tttatttaat aatttagata      3240
taaaatagaa taaaataaag tgactaaaaa ttaaacaaat ccctttaag aaattaaaaa        3300 aactaaggaa acattttct tgtttcgagt agataatgcc agcctgttaa acgccgccga        3360
cgagtctaac ggacaccaac cagcgaacca gcagcgtcgc gtcgggccaa gcgaagcaga      3420
cggcacggca tctctgtcgc tgcctctgga cccctctcga gagttccgct ccaccgttgg      3480
acttgctccg ctgtcggcat ccagaaattg cgtggcggag cggcagacgt gagccggcac      3540
ggcaggcggc ctcctcctcc tctcacggca ccggcagcta cgggggattc ctttcccacc      3600
gctccttcgc tttcccttcc tcgcccgccg taataaatag acaccccctc cacaccctct      3660
ttccccaacc tcgtgttgtt cggagcgcac acacacacaa ccagatctcc cccaaatcca      3720
cccgtcggca cctccgcttc aaggtacgcc gctcgtcctc cccccccccc cctctctacc      3780
ttctctagat cggcgttccg gtccatagtt agggcccggt agttctactt ctgttcatgt      3840
ttgtgttaga tccgtgtttg tgttagatcc gtgctgttag cgttcgtaca cggatgcgac      3900
ctgtacgtca gacacgttct gattgctaac ttgccagtgt ttctctttgg ggaatcctgg      3960
gatggctcta gccgttccgc agacgggatc gatttcatga ttttttttgt ttcgttgcat      4020
agggtttggt ttgccctttt cctttatttc aatatatgcc gtgcacttgt ttgtcgggtc      4080
atcttttcat gctttttttt gtcttggttg tgatgatgtg gtctggttgg gcggtcgttc      4140
tagatcggag tagaattctg tttcaaacta cctggtggat ttattaattt tggatctgta      4200
tgtgtgtgcc atacatattc atagttacga attgaagatg atggatggaa atatcgatct      4260
aggataggta tacatgttga tgcgggtttt actgatgcat atacagagat gcttttttgtt    4320 cgcttggttg tgatgatgtg gtgtggttgg gcggtcgttc attcgttcta gatcggagta     4380
gaatactgtt tcaaactacc tggtgtattt attaattttg gaactgtatg tgtgtgtcat      4440
acatcttcat agttacgagt ttaagatgga tggaaatatc gatctaggat aggtatacat      4500
gttgatgtgg gttttactga tgcatataca tgatggcata tgcagcatct attcatatgc      4560
tctaaccttg agtacctatc tattataata aacaagtatg ttttataatt attttgatct      4620
tgatatactt ggatgatggc atatgcagca gctatatgtg gatttttta gccctgcctt       4680 catacgctat ttatttgctt ggtactgttt cttttgtcga tgctcaccct gttgtttggt      4740
gttacttctg cagggatcca ccatgacggc cgacaacaac accgaggccc tggacagcag      4800
caccaccaag gacgtgatcc agaagggcat cagcgtggtg ggcgacctgc tgggcgtggt      4860
gggcttcccc ttcggcggcg ccctggtgag cttctacacc aacttcctga caccatctg      4920 gcccagcgag gaccctggaa ggccttcat ggagcaggtg gaggccctga tggaccagaa      4980
gatcgccgac tacgccaaga caaggcact ggccgagcta cagggcctcc agaacaacgt      5040
ggaggactat gtgagcgccc tgagcagctg gcagaagaac cccgctgcac cgttccgcaa      5100
cccccacagc cagggccgca tccgcgagct gttcagccag gccgagagcc acttccgcaa      5160
cagcatgccc agcttcgcca tcagcggcta cgaggtgctc ttcctgacca cctacgccca      5220
ggccgccaac acccacctgt tcctgctgaa ggacgcccaa atctacggag aggagtgggg      5280
```

```
ctacgagaag gaggacatcg ccgagttcta caagcgccag ctgaagctga cccaggagta    5340
caccgaccac tgcgtgaagt ggtacaacgt gggtctagac aagctccgcg gcagcagcta    5400
cgagagctgg gtgaacttca accgctaccg ccgcgagatg accctgaccg tgctggacct    5460
gatcgccctg ttccccctgt acgacgtgcg cctgtacccc aaggaggtga agaccgagct    5520
gacccgcgac gtgctgaccg accccatcgt gggcgtgaac aacctgcgcg gctacggcac    5580
caccttcagc aacatcgaga actacatccg caagccccac ctgttcgact acctgcaccg    5640
catccagttc cacacgcgtt ccagcccggc tactacggc aacgacagct caactactg     5700
gagcggcaac tacgtgagca cccgcccag catcggcagc aacgacatca tcaccagccc    5760
cttctacggc aacaagagca gcgagcccgt gcagaacctt gagttcaacg gcgagaaggt    5820
gtaccgcgcg gtggctaaca ccaacctggc cgtgtggccc tctgcagtgt acagcggcgt    5880
gaccaaggtg gagttcagcc agtacaacga ccagaccgac gaggccagca cccagaccta    5940
cgacagcaag cgcaacgtgg gcgccgtgag ctgggacagc atcgaccagc tgcccccga    6000
gaccaccgac gagcccctgg agaagggcta cagccaccag ctgaactacg tgatgtgctt    6060
cctgatgcag ggcagccgcg gcaccatccc cgtgctgacc tggacccaca gagcgtcga   6120
cttcttcaac atgatcgaca gcaagaagat cacccagctg cccctggtga aggcctacaa    6180
gctccagagc ggcgccagcg tggtggcagg cccccgcttc accggcggcg acatcatcca    6240
gtgcaccgag aacggcagcg ccgccaccat ctacgtgacc cccgacgtga gctacagcca    6300
gaagtaccgc gcccgcatcc actacgccag caccagccag atcaccttca ccctgagcct    6360
ggacggggcc cccttcaacc aatactactt cgacaagacc atcaacaagg gcgacaccct    6420
gacctacaac agcttcaacc tggccagctt cagcaccccct ttcgagctga gcggcaacaa    6480
cctccagatc ggcgtgaccg gcctgagcgc cggcgacaag gtgtacatcg acaagatcga    6540
gttcatcccc gtgaactaga tctgaggggg accagctctt gacgacctgc taagatcgtt    6600
caaacatttg gcaataaagt ttcttaagat tgaatcctgt tgccggtctt gcgatgatta    6660
tcaatataat ttctgttgaa ttacgttaag catgtaataa ttaacatgta atgcatgacg    6720
ttatttatga gatgggtttt tatgattaga gtcccgcaat tatacattta atacgcgata    6780
gaaaacaaaa tatagcgcgc aaactaggat aaattatcgc gcgcggtgtc atctattgtt    6840
actagatcta attgacggac ccggcgcgcc atttaaatgg taccggtccg gcatgcatgc    6900
agggatccac atggagtcaa agattcaaat agaggaccta acagaactcg ccgtaaagac    6960
tggcgaacag ttcatacaga gtctcttacg actcaatgca agaagaaaaa tcttcgtcaa    7020
catggtggag cacgacacgc ttgtctactc caaaaatatc aaagatacag tctcagaaga    7080
ccaaagggca attgagactt ttcaacaaag ggtaatatcc ggaaacctcc tcggattcca    7140
ttgcccagct atctgtcact ttattgtgaa gatagtggaa aaggaaggtg gctcctacaa    7200
atgccatcat tgcgataaag gaaaggccat cgttgaagat gcctctgccg acagtggtcc    7260
caaagatgga cccccaccca cgaggagcat cgtggaaaaa gaagacgttc caaccacgtc    7320
ttcaaagcaa gtggattgat gtgatatctc cactgacgta agggatgacg cacaatccca    7380
ctatccttcg caagaccctt cctctatata aggaagttca tttcatttgg agaggacacg    7440
ctgaaatcac tagtccacca tgtctccgga gaggagacca gttgagatta ggccagctac    7500
agcagctgat atgccgcgg tttgtgtatat cgttaaccat tacattgaga cgtctacagt    7560
gaactttagg acagagccac aaacaccaca agagtggatt gatgatctag agaggttgca    7620
```

```
agatagatac ccttggttgg ttgctgaggt tgagggtgtt gtggctggta ttgcttacgc    7680
tgggccctgg aaggctagga acgcttacga ttggacagtt gagagtactg tttacgtgtc    7740
acataggcat caaaggttgg gcctaggatc cacattgtac acacatttgc ttaagtctat    7800
ggaggcgcaa ggttttaagt ctgtggttgc tgttataggc cttccaaacg atccatctgt    7860
taggttgcat gaggctttgg gatacacagc gcggggtaca ttgcgcgcag ctggatacaa    7920
gcatggtgga tggcatgatg ttggtttttg gcaaagggat tttgagttgc cagctcctcc    7980
aaggccagtt aggccagtta cccagatctg aatagtgata tcggcgcctg ggtcgacctg    8040
cagatcgttc aaacatttgg caataaagtt tcttaagatt gaatcctgtt gccggtcttg    8100
cgatgattat catataattt ctgttgaatt acgttaagca tgtaataatt aacatgtaat    8160
gcatgacgtt atttatgaga tgggttttta tgattagagt cccgcaatta tacatttaat    8220
acgcgataga aaacaaaata tagcgcgcaa actaggataa attatcgcgc gcggtgtcat    8280
ctatgttact agatc                                                     8295
```

<210> SEQ ID NO 2
<211> LENGTH: 13821
<212> TYPE: DNA
<213> ORGANISM: Artificial Sequence
<220> FEATURE:
<223> OTHER INFORMATION: Source organisms include Cestrum Yellows Leaf
      Curl Virus, Bacillus thuringiensis, Agrobacterium tumefaciens, Zea
      mays, Cauliflower Mosaic VirusStreptomyces viridochromogenes, and
      Escherichia coli.

<400> SEQUENCE: 2

```
attcctgtgg ttggcatgca catacaaatg gacgaacgga taaaccttttt cacgcccttt     60 taaatatccg attattctaa taaacgctct tttctcttag gtttacccgc caatatatcc    120
tgtcaaacac tgatagttta aactggcact agcctaacgg tgttgactaa gtaggccgct    180
tccctaatta gctaagggac ccgggtcatt gagcggagaa ttaagggagt cacgttatga    240
cccccgccga tgacgcggga caagccgttt tacgtttgga actgacagaa ccgcaacgaa    300
tattggcaga caaagtggca gacatactgt cccacaaatg aagatggaat ctgtaaaaga    360
aaacgcgtga ataatgcgt ctgacaaagg ttaggtcggc tgcctttaat caataccaaa    420
gtggtcccta ccacgatgga aaaactgtgc agtcggtttg ctttttctg acgaacaaat    480 aagattcgtg gccgacaggt gggggtccac catgtgaagg catcttcaga ctccaataat    540
ggagcaatga cgtaagggct tacgaaataa gtaaggggtag tttgggaaat gtccactcac    600
ccgtcagtct ataaatactt agcccctccc tcattgttaa gggagcaaaa tctcagagag    660
atagtcctag agagagaaag agagcaagta gcctagaagt ggatccacca tgactagtaa    720
cggccgccag tgtgctggta ttcgccctta tgacggccga caacaacacc gaggcctgga    780
cagcagcacc accaaggacg tgatccagaa gggcatcagc gtggtgggcg acctgctggg    840
cgtggtgggc ttccccttcg gcggcgccct ggtgagcttc tacaccaact tcctgaacac    900
catctggccc agcgaggacc cctggaaggc cttcatggag caggtggagg ccctgatgga    960
ccagaagatc gccgactacg ccaagaacaa ggcactggcc gagctacagg gcctccagaa   1020
caacgtggag gactatgtga cgccctgag cagctggcag aagaacccg ctgcaccgtt   1080 ccgcaacccc cacagccagg gccgcatccg cgagctgttc agccaggccg agagccactt   1140
ccgcaacagc atgcccagct cgcatcag cggctacgag gtgctgttcc tgaccaccta   1200
cgcccaggcc gccaacaccc acctgttcct gctgaaggac gcccaaatct acggagagga   1260
```

```
gtggggctac gagaaggagg acatcgccga gttctacaag cgccagctga agctgaccca   1320
ggagtacacc gaccactgcg tgaagtggta caacgtgggt ctagacaagc tccgcggcag   1380
cagctacgag agctgggtga acttcaaccg ctaccgccgc gagatgaccc tgaccgtgct   1440
ggacctgatc gccctgttcc ccctgtacga cgtgcgcctg tacccaaggg aggtgaagac   1500
cgagctgacc cgcgacgtgc tgaccgaccc catcgtgggc gtgaacaacc tgcgcggcta   1560
cggcaccacc ttcagcaaca tcgagaacta catccgcaag ccccacctgt tcgactacct   1620
gcaccgcatc cagttccaca cgcgtttcca gcccggctac tacggcaacg acagcttcaa   1680
ctactggagc ggcaactacg tgagcacccg ccccagcatc ggcagcaacg acatcatcac   1740
cagcccttc tacggcaaca agagcagcga gcccgtgcag aaccttgagt tcaacggcga   1800
gaaggtgtac cgcgccgtgg ctaacaccaa cctggccgtg tggccctctg cagtgtacag   1860
cggcgtgacc aaggtggagt tcagccagta caacgaccag accgacgagg ccagcaccca   1920
gacctacgac agcaagcgca acgtgggcgc cgtgagctgg acagcatcg accagctgcc   1980
ccccgagacc accgacgagc ccctggagaa gggctacagc caccagctga actacgtgat   2040
gtgcttcctg atgcagggca gccgcggcac catccccgtg ctgacctgga cccacaagag   2100
cgtcgacttc ttcaacatga tcgacagcaa gaagatcacc cagctgcccc tgaccaagag   2160
caccaacctg ggcagcggca ccagcgtggt gaagggcccc ggcttcaccg gcggcgacat   2220
cctgcgccgc accagccccg gccagatcag caccctgcgc gtgaacatca ccgcccccct   2280
gagccagcgc taccgcgtcc gcatccgcta cgccagcacc accaacctgc agttccacac   2340
cagcatcgac ggccgcccca tcaaccaggg caacttcagc gccaccatga gcagcggcag   2400
caacctgcag agcggcagct tccgcaccgt gggcttcacc acccccttca acttcagcaa   2460
cggcagcagc gtgttcaccc tgagcgccca cgtgttcaac agcggcaacg aggtgtacat   2520
cgaccgcatc gagttcgtgc ccgccgaggt gaccttcgag gccgagtacg acctggagag   2580
ggctcagaag gccgtgaacg agctgttcac cagcagcaac cagatcggcc tgaagaccga   2640
cgtgaccgac taccacatcg atcaggtgta ggagctgagc tcttcatatg acgatcgttc   2700
aaacatttgg caataaagtt tcttaagatt gaatcctgtt gccggtcttg cgatgattat   2760
catataattt ctgttgaatt acgttaagca tgtaataatt aacatgtaat gcatgacgtt   2820
atttatgaga tgggttttta tgattagagt cccgcaatta tacatttaat acgcgataga   2880
aaacaaaata tagcgcgcaa actaggataa attatcgcgc gcggtgtcat ctatgttact   2940
agatcgcgga cccaagcttg catgcctgca gtgcagcgtg accggtcgt gcccctctct   3000
agagataatg agcattgcat gtctaagtta taaaaaatta ccacatattt ttttttgtcac   3060
acttgtttga agtgcagttt atctatcttt atacatatat ttaaacttta ctctacgaat   3120
aatataatct atagtactac aataatatca gtgttttaga gaatcatata aatgaacagt   3180
tagacatggt ctaaaggaca attgagtatt ttgacaacag gactctacag ttttatcttt   3240
ttagtgtgca tgtgttctcc ttttttttg caaatagctt cacctatata atacttcatc   3300
catttattta gtacatccat ttagggtttta gggttaatgg ttttatagac taatttttt   3360
tagtacatct attttattct attttagcct ctaaattaag aaaactaaaa ctctatttta   3420
gtttttttat ttaataattt agatataaaa tagaataaaa taaagtgact aaaaattaaa   3480
caaataccct ttaagaaatt aaaaaaacta aggaaacatt tttcttgttt cgagtagata   3540
atgccagcct gttaaacgcc gccgacgagt ctaacgacca ccaaccagcg aaccagcagc   3600
gtcgcgtcgg gccaagcgaa gcagacggca cggcatctct gtcgctgcct ctggacccct   3660
```

```
ctcgagagtt ccgctccacc gttggacttg ctccgctgtc ggcatccaga aattgcgtgg    3720
cggagcggca gacgtgagcc ggcacggcag gcggcctcct cctcctctca cggcaccggc    3780
agctacgggg gattcctttc ccaccgctcc ttcgctttcc cttcctcgcc cgccgtaata    3840
aatagacacc ccctccacac cctctttccc caacctcgtg ttgttcggag cgcacacaca    3900
cacaaccaga tctcccccaa atccacccgt cggcacctcc gcttcaaggt acgccgctcg    3960
tcctcccccc cccccctct ctaccttctc tagatcggcg ttccggtcca tagttagggc    4020
ccggtagttc tacttctgtt catgtttgtg ttagatccgt gtttgtgtta gatccgtgct    4080
gttagcgttc gtacacggat gcgacctgta cgtcagacac gttctgattg ctaacttgcc    4140
agtgtttctc tttggggaat cctgggatgg ctctagccgt tccgcagacg ggatcgattt    4200
catgattttt tttgtttcgt tgcatagggt ttggtttgcc cttttccttt atttcaatat    4260
atgccgtgca cttgtttgtc gggtcatctt ttcatgcttt tttttgtctt ggttgtgatg    4320
atgtggtctg gttgggcggt cgttctagat cggagtagaa ttctgtttca aactacctgg    4380
tggatttatt aattttggat ctgtatgtgt gtgccataca tattcatagt tacgaattga    4440
agatgatgga tggaaatatc gatctaggat aggtatacat gttgatgcgg gttttactga    4500
tgcatataca gagatgcttt ttgttcgctt ggttgtgatg atgtggtgtg gttgggcggt    4560
cgttcattcg ttctagatcg gagtagaata ctgtttcaaa ctacctggtg tatttattaa    4620
ttttggaact gtatgtgtgt gtcatacatc ttcatagtta cgagtttaag atggatggaa    4680
atatcgatct aggataggta tacatgttga tgtgggtttt actgatgcat atacatgatg    4740
gcatatgcag catctattca tatgctctaa ccttgagtac ctatctatta taataaacaa    4800
gtatgtttta taattatttt gatcttgata tacttggatg atggcatatg cagcagctat    4860
atgtggattt ttttagccct gccttcatac gctatttatt tgcttggtac tgtttctttt    4920
gtcgatgctc accctgttgt ttggtgttac ttctgcaggg atccaccatg acggccgaca    4980
acaacaccga ggccctggac agcagcacca ccaaggacgt gatccagaag ggcatcagcg    5040
tggtgggcga cctgctgggc gtggtgggct tccccttcgg cggcgccctg gtgagcttct    5100
acaccaactt cctgaacacc atctggccca gcgaggaccc ctggaaggcc ttcatggagc    5160
aggtggaggc cctgatggac cagaagatcg ccgactacgc caagaacaag gcactggccg    5220
agctacaggg cctccagaac aacgtggagg actatgtgag cgccctgagc agctggcaga    5280
agaaccccgc tgcaccgttc cgcaaccccc acagccaggg ccgcatccgc gagctgttca    5340
gccaggccga gagccacttc cgcaacagca tgcccagctt cgccatcagc ggctacgagg    5400
tgctgttcct gaccacctac gcccaggccg ccaacaccca cctgttcctg ctgaaggacg    5460
cccaaatcta cggagaggag tggggctacg agaaggagga catcgccgag ttctacaagc    5520
gccagctgaa gctgacccag gagtacaccg accactgcgt gaagtggtac aacgtgggtc    5580
tagacaagct ccgcggcagc agctacgaga gctgggtgaa cttcaaccgc taccgccgcg    5640
agatgaccct gaccgtgctg gacctgatcg ccctgttccc cctgtacgac gtgcgcctgt    5700
accccaagga ggtgaagacc gagctgaccc gcgacgtgct gaccgacccc atcgtgggcg    5760
tgaacaacct gcgcggctac ggcaccacct tcagcaacat cgagaactac atccgcaagc    5820
cccacctgtt cgactacctg caccgcatcc agttccacac gcgtttccag cccggctact    5880
acggcaacga cagcttcaac tactggacgc gcaactacgt gagcacccgc ccagcatcg    5940 gcagcaacga catcatcacc agcccccttct acggcaacaa gagcagcgag cccgtgcaga    6000
```

-continued

```
accttgagtt caacggcgag aaggtgtacc gcgccgtggc taacaccaac ctggccgtgt    6060
ggccctctgc agtgtacagc ggcgtgacca aggtggagtt cagccagtac aacgaccaga    6120
ccgacgaggc cagcacccag acctacgaca gcaagcgcaa cgtgggcgcc gtgagctggg    6180
acagcatcga ccagctgccc cccgagacca ccgacgagcc cctggagaag ggctacagcc    6240
accagctgaa ctacgtgatg tgcttcctga tgcagggcag ccgcggcacc atccccgtgc    6300
tgacctggac ccacaagagc gtcgacttct caacatgat cgacagcaag aagatcaccc     6360
agctgcccct ggtgaaggcc tacaagctcc agagcggcgc cagcgtggtg gcaggccccc    6420
gcttcaccgg cggcgacatc atccagtgca ccgagaacgg cagcgccgcc accatctacg    6480
tgaccccga cgtgagctac agccagaagt accgcgcccg catccactac gccagcacca    6540
gccagatcac cttcaccctg agcctggacg ggccccctt caaccaatac tacttcgaca    6600
agaccatcaa caagggcgac accctgacct acaacagctt caacctggcc agcttcagca    6660
ccccttcga gctgagcggc aacaacctcc agatcggcgt gaccggcctg agcgccggcg    6720
acaaggtgta catcgacaag atcgagttca tccccgtgaa ctagatctga ggggtaccag    6780
ctcttgacga cctgctaaga tcgttcaaac atttggcaat aaagtttctt aagattgaat    6840
cctgttgccg gtcttgcgat gattatcaat ataatttctg ttgaattacg ttaagcatgt    6900
aataattaac atgtaatgca tgacgttatt tatgagatgg gttttatga ttagagtccc     6960
gcaattatac atttaatacg cgatagaaaa caaaatatag cgcgcaaact aggataaatt    7020
atcgcgcgcg gtgtcatcta ttgttactag atctaattga cggacccggc gcgccattta    7080
aatggtaccg gtccggcatg catgcaggga tccacatgga gtcaaagatt caaatagagg    7140
acctaacaga actcgccgta aagactggcg aacagttcat acagagtctc ttacgactca    7200
atgacaagaa gaaaatcttc gtcaacatgg tggagcacga cacgcttgtc tactccaaaa    7260
atatcaaaga tacagtctca gaagaccaaa gggcaattga acttttcaa caaagggtaa    7320
tatccggaaa cctcctcgga ttccattgcc cagctatctg tcactttatt gtgaagatag    7380
tggaaaagga aggtggctcc tacaaatgcc atcattgcga taaggaaag gccatcgttg    7440
aagatgcctc tgccgacagt ggtcccaaag atggaccccc acccacgagg agcatcgtgg    7500
aaaaagaaga cgttccaacc acgtcttcaa agcaagtgga ttgatgtgat atctccactg    7560
acgtaaggga tgacgcacaa tcccactatc cttcgcaaga cccttcctct atataaggaa    7620
gttcatttca tttggagagg acacgctgaa atcactagtc accatgtct ccggagagga     7680
gaccagttga gattaggcca gctacagcag ctgatatggc cgcggtttgt gatatcgtta    7740
accattacat tgagacgtct acagtgaact ttaggacaga gccacaaaca ccacaagagt    7800
ggattgatga tctagagagg ttgcaagata gataccttg gttggttgct gaggttgagg     7860
gtgttgtggc tggtattgct tacgctgggc cctggaaggc taggaacgct tacgattgga    7920
cagttgagag tactgtttac gtgtcacata ggcatcaaag gttgggccta ggatccacat    7980
tgtacacaca tttgcttaag tctatggagg cgcaaggttt taagtctgtg gttgctgtta    8040
taggccttcc aaacgatcca tctgttaggt tgcatgaggc tttgggatac acagcgcggg    8100
gtacattgcg cgcagctgga tacaagcatg gtggatggca tgatgttggt ttttggcaaa    8160
gggattttga gttgccagct cctccaaggc cagttaggcc agttacccag atctgaatag    8220
tgatatcggc gcctgggtcg acctgcagat cgttcaaaca tttggcaata aagtttctta    8280
agattgaatc ctgttgccgg tcttgcgatg attatcatat aatttctgtt gaattacgtt    8340
aagcatgtaa taattaacat gtaatgcatg acgttattta tgagatgggt ttttatgatt    8400
```

```
agagtcccgc aattatacat ttaatacgcg atagaaaaca aaatatagcg cgcaaactag    8460
gataaattat cgcgcgcggt gtcatctatg ttactagatc cgtagccctg caggaaattt    8520
accggtgccc gggcggccag catggccgta tccgcaatgt gttattaagt tgtctaagcg    8580
tcaatttgtt tacaccacaa tatatcctgc caccagccag ccaacagctc cccgaccggc    8640
agctcggcac aaaatcacca ctcgatacag gcagcccatc agaattaatt ctcatgtttg    8700
acagcttatc atcgactgca cggtgcacca atgcttctgg cgtcaggcag ccatcggaag    8760
ctgtggtatg gctgtgcagg tcgtaaatca ctgcataatt cgtgtcgctc aaggcgcact    8820
cccgttctgg ataatgtttt ttgcgccgac atcataacgg ttctggcaaa tattctgaaa    8880
tgagctgttg acaattaatc atccggctcg tataatgtgt ggaattgtga gcggataaca    8940
atttcacaca ggaaacagac catgagggaa gcgttgatcg ccgaagtatc gactcaacta    9000
tcagaggtag ttggcgtcat cgagcgccat ctcgaaccga cgttgctggc cgtacatttg    9060
tacggctccg cagtggatgg cggcctgaag ccacacagtg atattgattt gctggttacg    9120
gtgaccgtaa ggcttgatga acaacgcgg cgagctttga tcaacgacct tttggaaact    9180
tcggcttccc ctggagagag cgagattctc cgcgctgtag aagtcaccat tgttgtgcac    9240
gacgacatca ttccgtggcg ttatccagct aagcgcgaac tgcaatttgg agaatggcag    9300
cgcaatgaca ttcttgcagg tatcttcgag ccagccacga tcgacattga tctggctatc    9360
ttgctgacaa aagcaagaga acatagcgtt gccttggtag gtccagcggc ggaggaactc    9420
tttgatccgg ttcctgaaca ggatctattt gaggcgctaa atgaaacctt aacgctatgg    9480
aactcgccgc ccgactgggc tggcgatgag cgaaatgtag tgcttacgtt gtcccgcatt    9540
tggtacagcg cagtaaccgg caaaatcgcg ccgaaggatg tcgctgccga ctgggcaatg    9600
gagcgcctgc cggcccagta tcagcccgtc atacttgaag ctaggcaggc ttatcttgga    9660
caagaagatc gcttggcctc gcgcgcagat cagttggaag aatttgttca ctacgtgaaa    9720
ggcgagatca ccaaagtagt cggcaaataa agctctagtg gatctccgta cccagggatc    9780
tggctcgcgg cggacgcacg acgccggggc gagaccatag gcgatctcct aaatcaatag    9840
tagctgtaac ctcgaagcgt ttcacttgta acaacgattg agaattttg tcataaaatt     9900 gaaatacttg gttcgcattt ttgtcatccg cggtcagccg caattctgac gaactgccca    9960
tttagctgga gatgattgta catccttcac gtgaaaattt ctcaagcgct gtgaacaagg   10020
gttcagattt tagattgaaa ggtgagccgt tgaaacacgt tcttcttgtc gatgacgacg   10080
tcgctatgcg gcatcttatt attgaatacc ttacgatcca cgccttcaaa gtgaccgcgg   10140
tagccgacag cacccagttc acaagagtac tctcttccgc gacggtcgat gtcgtggttg   10200
ttgatctaga tttaggtcgt gaagatgggc tcgagatcgt tcgtaatctg gcggcaaagt   10260
ctgatattcc aatcataatt atcagtggcg accgccttga ggagacggat aaagttgttg   10320
cactcgagct aggagcaagt gattttatcg ctaagccgtt cagtatcaga gagtttctag   10380
cacgcattcg ggttgccttg cgcgtgcgcc ccaacgttgt ccgctccaaa gaccgacggt   10440 cttttttgttt tactgactgg acacttaatc tcaggcaacg tcgcttgatg tccgaagctg   10500
gcggtgaggt gaaacttacg gcaggtgagt tcaatcttct cctcgcgttt ttagagaaac   10560
cccgcgacgt tctatcgcgc gagcaacttc tcattgccag tcgagtacgc gacgaggagg   10620
tttatgacag gagtatagat gttctcattt tgaggctgcg ccgcaaactt gaggcagatc   10680
cgtcaagccc tcaactgata aaaacagcaa gaggtgccgg ttatttcttt gacgcggacg   10740
```

```
tgcaggtttc gcacgggggg acgatggcag cctgagccaa ttcccagatc cccgaggaat    10800
cggcgtgagc ggtcgcaaac catccggccc ggtacaaatc ggcgcggcgc tgggtgatga    10860
cctggtggag aagttgaagg ccgcgcaggc cgcccagcgg caacgcatcg aggcagaagc    10920
acgccccggt gaatcgtggc aagcggccgc tgatcgaatc cgcaaagaat cccggcaacc    10980
gccggcagcc ggtgcgccgt cgattaggaa gccgcccaag ggcgacgagc aaccagattt    11040
tttcgttccg atgctctatg acgtgggcac ccgcgatagt cgcagcatca tggacgtggc    11100
cgttttccgt ctgtcgaagc gtgaccgacg agctggcgag gtgatccgct acgagcttcc    11160
agacgggcac gtagaggttt ccgcaggcc ggccggcatg gccagtgtgt gggattacga    11220
cctggtactg atggcggttt cccatctaac cgaatccatg aaccgatacc gggaagggaa    11280
gggagacaag cccggccgcg tgttccgtcc acacgttgcg gacgtactca agttctgccg    11340
gcgagccgat ggcggaaagc agaaagacga cctggtagaa acctgcattc ggttaaacac    11400
cacgcacgtt gccatgcagc gtacgaagaa ggccaagaac ggccgcctgg tgacggtatc    11460
cgagggtgaa gccttgatta gccgctacaa gatcgtaaag agcgaaaccg ggcggccgga    11520
gtacatcgag atcgagctgg ctgattggat gtaccgcgag atcacagaag caagaaccc    11580 ggacgtgctg acggttcacc ccgattactt tttgatcgat cccggcatcg gccgttttct    11640
ctaccgcctg gcacgccgcg ccgcaggcaa ggcagaagcc agatggttgt tcaagacgat    11700
ctacgaacgc agtggcagcg ccggagagtt caagaagttc tgtttcaccg tgcgcaagct    11760
gatcgggtca aatgacctgc cggagtacga tttgaaggag gaggcggggc aggctggccc    11820
gatcctagtc atgcgctacc gcaacctgat cgagggcgaa gcatccgccg gttcctaatg    11880
tacggagcag atgctagggc aaattgccct agcaggggaa aaaggtcgaa aaggtctctt    11940
tcctgtggat agcacgtaca ttgggaaccc aaagccgtac attgggaacc ggaaccgta    12000 cattgggaac ccaaagccgt acattgggaa ccggtcacac atgtaagtga ctgatataaa    12060
agagaaaaaa ggcgattttt ccgcctaaaa ctctttaaaa cttattaaaa ctcttaaaac    12120
ccgcctggcc tgtgcataac tgtctggcca gcgcacagcc gaagagctgc aaaaagcgcc    12180 taccttcgg tcgctgcgct ccctacgccc cgccgcttcg cgtcggccta tcgcggccgc    12240
tggccgctca aaaatggctg gcctacggcc aggcaatcta ccagggcgcg gacaagccgc    12300
gccgtcgcca ctcgaccgcc ggcgctgagg tctgcctcgt gaagaaggtg ttgctgactc    12360
ataccaggcc tgaatcgccc catcatccag ccagaaagtg agggagccac ggttgatgag    12420
agctttgttg taggtggacc agttggtgat tttgaacttt tgctttgcca cggaacggtc    12480
tgcgttgtcg ggaagatgcg tgatctgatc cttcaactca gcaaaagttc gatttattca    12540
acaaagccgc cgtcccgtca agtcagcgta atgctctgcc agtgttacaa ccaattaacc    12600
aattctgatt agaaaaactc atcgagcatc aaatgaaact gcaatttatt catatcagga    12660
ttatcaatac catattttg aaaaagccgt ttctgtaatg aaggagaaaa ctcaccgagg    12720
cagttccata ggatggcaag atcctggtat cggtctgcga ttccgactcg tccaacatca    12780
atacaaccta ttaatttccc ctcgtcaaaa ataaggttat caagtgagaa atcaccatga    12840
gtgacgactg aatccggtga gaatggcaaa agctctgcat taatgaatcg gccaacgcgc    12900
ggggagaggc ggtttgcgta ttgggcgctc ttccgcttcc tcgctcactg actcgctgcg    12960
ctcggtcgtt cggctgcggc gagcggtatc agctcactca aaggcggtaa tacggttatc    13020
cacagaatca ggggataacg caggaaagaa catgtgagca aaaggccagc aaaaggccag    13080
gaaccgtaaa aaggccgcgt tgctggcgtt tttccatagg ctccgccccc ctgacgagca    13140
```

```
tcacaaaaat cgacgctcaa gtcagaggtg gcgaaacccg acaggactat aaagatacca  13200
ggcgtttccc cctggaagct ccctcgtgcg ctctcctgtt ccgaccctgc cgcttaccgg  13260
atacctgtcc gcctttctcc cttcgggaag cgtggcgctt tctcatagct cacgctgtag  13320
gtatctcagt tcggtgtagg tcgttcgctc caagctgggc tgtgtgcacg aaccccccgt  13380
tcagcccgac cgctgcgcct tatccggtaa ctatcgtctt gagtccaacc cggtaagaca  13440
cgacttatcg ccactggcag cagccactgg taacaggatt agcagagcga ggtatgtagg  13500
cggtgctaca gagttcttga agtggtggcc taactacggc tacactagaa gaacagtatt  13560
tggtatctgc gctctgctga agccagttac cttcggaaaa agagttggta gctcttgatc  13620
cggcaaacaa accaccgctg gtagcggtgg ttttttgtt tgcaagcagc agattacgcg  13680
cagaaaaaaa ggatctcaag aagatcccttt gatcttttct acggggtctg acgctcagtg  13740
gaacgaaaac tcacgttaag ggatttggt catgagatta tcaaaaagga tcttcaccta  13800
gatccttttg atccggaatt a                                            13821
```